(12) United States Patent  (10) Patent No.: US 9,247,866 B2
Aferzon  (45) Date of Patent: Feb. 2, 2016

(54) ROTATIONAL STABILIZING LOCKING MECHANISM

(71) Applicant: Joshua Aferzon, Stamford, CT (US)

(72) Inventor: Joshua Aferzon, Stamford, CT (US)

( * ) Notice: Subject to any disclaimer, the term of this patent is extended or adjusted under 35 U.S.C. 154(b) by 0 days.

(21) Appl. No.: 13/833,759

(22) Filed: Mar. 15, 2013

(65) Prior Publication Data

US 2013/0281791 A1  Oct. 24, 2013

Related U.S. Application Data

(60) Provisional application No. 61/636,818, filed on Apr. 23, 2012.

(51) Int. Cl.
| | | |
|---|---|---|
| *A61B 1/32* | (2006.01) | |
| *A61B 1/06* | (2006.01) | |
| *A61B 17/02* | (2006.01) | |
| *A61B 1/313* | (2006.01) | |
| *A61B 19/00* | (2006.01) | |

(52) U.S. Cl.
CPC .............. *A61B 1/06* (2013.01); *A61B 17/0293* (2013.01); *A61B 1/3132* (2013.01); *A61B 2019/5206* (2013.01)

(58) Field of Classification Search
CPC ........................... A61B 17/02; A61B 17/0293
USPC .................................................. 600/185–249
See application file for complete search history.

(56) References Cited

U.S. PATENT DOCUMENTS

| | | | |
|---|---|---|---|
| 3,762,400 A * | 10/1973 | McDonald ..................... 600/212 |
| 4,883,426 A | 11/1989 | Ferrer | |
| 5,125,396 A | 6/1992 | Ray | |
| 5,509,893 A * | 4/1996 | Pracas ........................... 600/224 |
| 7,491,168 B2 | 2/2009 | Raymond et al. | |
| 7,892,174 B2 | 2/2011 | Hestad et al. | |
| 8,303,497 B2 | 11/2012 | Aferzon | |
| 8,636,657 B2 * | 1/2014 | Hamada ........................ 600/233 |
| 2005/0070765 A1 * | 3/2005 | Abdelgany et al. ........... 600/214 |
| 2006/0224044 A1 | 10/2006 | Marchek et al. | |
| 2006/0235279 A1 | 10/2006 | Hawkes et al. | |

(Continued)

OTHER PUBLICATIONS

International Preliminary Report on Patentability issued in International Application No. PCT/US2013/037857, having a mailing date of Aug. 21 2013.

(Continued)

*Primary Examiner* — Jerry Cumberledge
*Assistant Examiner* — Tessa Matthews
(74) *Attorney, Agent, or Firm* — The Marbury Law Group, PLLC

(57) ABSTRACT

A rotational stabilizing locking apparatus for a surgical retractor is disclosed. The, rotational stabilizing locking apparatus may be a locking cap that includes a central body having a surgical aperture extending from a first side of the central body to a second opposed side of the central body. The central body may include an attachment arm extending away from the surgical aperture. Also, a first interfacing prong may extend from the first side of the central body. The first interfacing prong may include a first light source guide element along an extent of the first interfacing prong. Additionally, the locking cap may be applied to an inner arcuate blade nested inside an outer arcuate blade having a coupling aperture. The inner arcuate blade may include a prong slot for receiving the first interfacing prong. Also, a coupling tab of the inner arcuate blade may be disposed within the coupling aperture.

33 Claims, 17 Drawing Sheets

(56) References Cited

U.S. PATENT DOCUMENTS

| | | |
|---|---|---|
| 2007/0088277 A1 | 4/2007 | McGinley et al. |
| 2007/0208229 A1 | 9/2007 | Prusmack |
| 2007/0282171 A1* | 12/2007 | Karpowicz et al. ............ 600/224 |
| 2009/0069634 A1* | 3/2009 | Larkin ............................ 600/222 |
| 2009/0093684 A1* | 4/2009 | Schorer ......................... 600/210 |
| 2010/0240961 A1* | 9/2010 | Aferzon ......................... 600/212 |
| 2011/0021882 A1* | 1/2011 | Selover et al. ................. 600/245 |
| 2012/0245431 A1 | 9/2012 | Baudouin et al. |
| 2012/0259177 A1 | 10/2012 | Fiorella |

OTHER PUBLICATIONS

International Preliminary Report on Patentability issued for International Application No. PCT/US2013/037857, mailed on Nov. 6, 2014.

\* cited by examiner

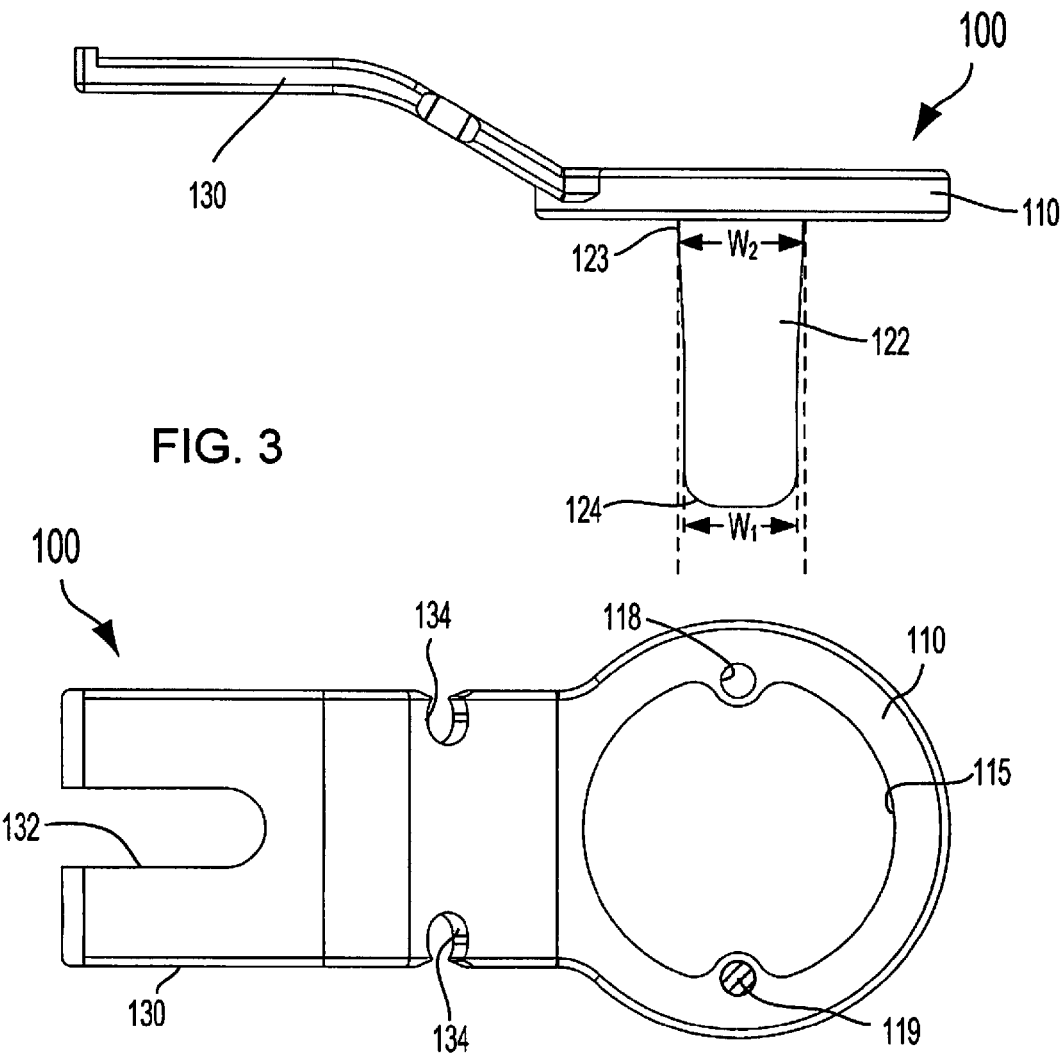

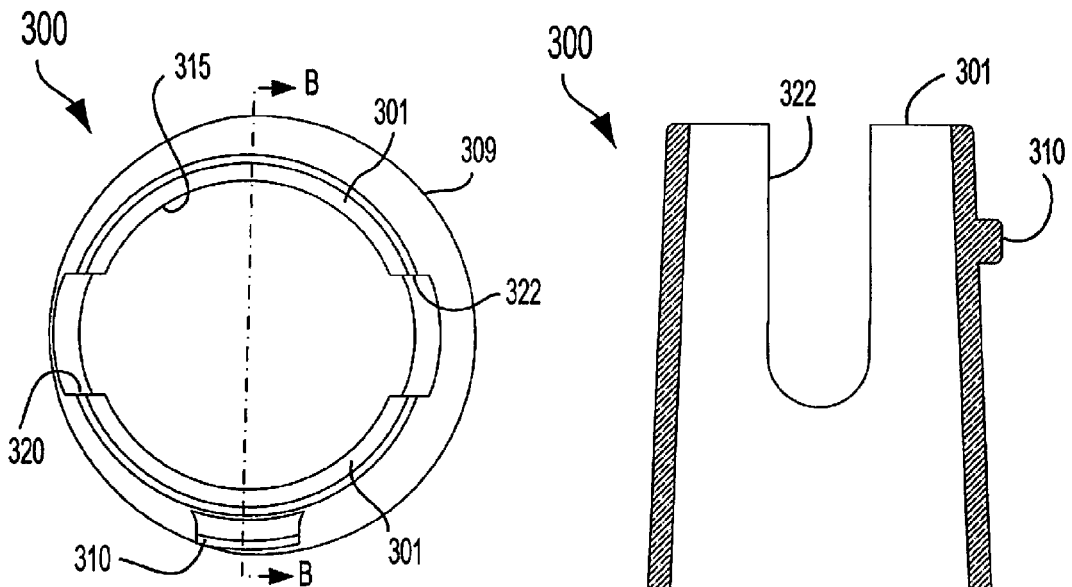
FIG. 11
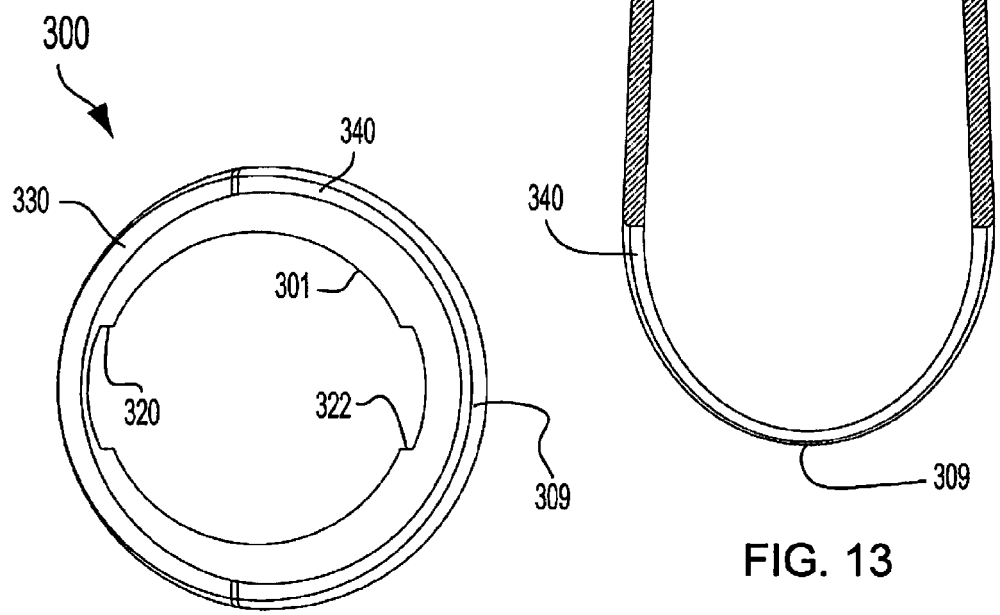
FIG. 12
FIG. 13

ROTATIONAL STABILIZING LOCKING MECHANISM

RELATED APPLICATIONS

The present non-provisional patent application claims the benefit of priority to U.S. Provisional Patent Application No. 61/636,818 filed Apr. 23, 2012 to the same inventor, the entire contents of which are hereby incorporated by reference.

BACKGROUND

The present disclosure relates to rotational stabilizing locking mechanisms for orthopedic instrumentation, including a surgical retractor. Devices that incorporate rotational displacement in their function often require locking or stabilization once a desired position is achieved. Although rotational mechanisms vary greatly in design, most function by spherical or cylindrical motion. In medical device applications, many technologies utilize tubular or spherical geometries to either mimic natural anatomy, provide stability, or prepare pathways in a surgical field.

Endoscopic tubular retractors are instruments utilized by surgeons to dilate tissue, such as muscle, and prepare surgical pathways for minimizing the invasive nature of surgery. Traditionally, surgical instruments are designed to withstand muscular tension and facilitate visualization. Additionally, more than one dilator may be used, with gradually increasing diameters, to slowly spread the tissue and prepare an operative space. Current deep-cavity surgical technologies, including retractors, are limited in their visualization capabilities.

SUMMARY

In an embodiment, a surgical retractor with rotational stabilizing locking apparatus for providing access to a surgical cavity is disclosed. The rotational stabilizing locking apparatus may include a central body with a surgical aperture extending from a first side of the central body to a second opposed side of the central body. The central body may include an attachment arm extending away from the surgical aperture. Also, a first interfacing prong may be provided extending from the first side of the central body. The first interfacing prong may include a first light source guide element along an extent of the first interfacing prong.

In one or more embodiments, the rotational stabilizing locking apparatus may include a second interfacing prong extending from the first side of the central body. The second interfacing prong may be disposed remote from the first interfacing prong. Also, the second interfacing prong may include a second light source guide element extending lengthwise along the second interfacing prong. The first light source guide element may include a channel extending away from the first side of the central body for receiving a first light source conductor. Also, the channel may include a tubular passageway for holding the first light source conductor. A first light source conductor may be retained by the first light source guide element. The first light source conductor may extend from the central body toward a remote distal end of the first interfacing prong. Further, the attachment arm may be configured to interface with a mounting structure and may include at least one mounting aperture extending through the attachment arm. The first interfacing prong may include a proximal end adjoining the central body and an opposed distal end, wherein the opposed distal end includes a first width and the proximal end includes a second width. The second width may be wider than the first width for frictionally securing the central body to a surgical retractor blade. Also, the central body may include an annular shape having the surgical aperture extending there through.

Additionally in one or more embodiments, an outer arcuate blade may include a first proximal end and an opposed first distal end. An outer arcuate blade may include a coupling aperture and an inner arcuate blade may be in sliding engagement with the outer arcuate blade. The inner arcuate blade may include a prong slot for receiving the first interfacing prong. Also, the inner arcuate blade may include a second proximal end and an opposed second distal end. Additionally, the inner arcuate blade may include a coupling tab configured to be disposed within the coupling aperture. The first proximal end and the second proximal end may be disposed adjacent the central body. Further, the first interfacing prong may be configured to travel along the prong slot until seated therein, providing a pressure fitting between the inner arcuate blade and the first interfacing prong and rotationally locking the central body relative to the inner arcuate blade and the outer arcuate blade. Further still, at least one of the first proximal end and the second proximal end may include an annular shape. Similarly, the outer arcuate blade and the inner arcuate blade may each form a truncated conical shape, having the inner arcuate blade being partially surrounded by the outer arcuate blade.

One or more embodiment may have the coupling tab prevent the inner arcuate blade from being fully inserted inside the outer arcuate blade without deforming at least one of the outer arcuate blade and the inner arcuate blade. Deforming at least one of the outer arcuate blade and the inner arcuate blade may be accomplished by deforming the second proximal end and temporarily constricting the prong slot. Also, a curvature of the surgical aperture may be sized to match an inner arcuate wall of the inner arcuate blade.

Another embodiment includes a surgical retractor with rotational stabilizing locking apparatus. The surgical retractor may include an outer arcuate blade having a first proximal end and an opposed first distal end. The outer arcuate blade may include a coupling aperture. An inner arcuate blade may be in sliding engagement with the outer arcuate blade. Also, the inner arcuate blade may include a first prong slot forming a first gap extending through a full thickness of the inner arcuate blade. Additionally, the inner arcuate blade may include a second proximal end, an opposed second distal end and a coupling tab configured to be disposed within the coupling aperture. The comprising rotational stabilizing locking apparatus may include a central body having an attachment arm extending away from the outer arcuate blade and the inner arcuate blade. Also, a first interfacing prong may extend from the central body into the first prong slot.

In addition, the inner arcuate blade may include a second prong slot forming a second gap extending through the full thickness of the inner arcuate blade. The second prong slot may be disposed remote from the first prong slot, wherein the rotational stabilizing locking mechanism may further include a second interfacing prong extending from the central body into the second prong slot. Also, at least one of the first interfacing prong and the second interfacing prong may include a light source guide element for retaining a light source conductor extending from the central body toward the opposed first distal end and the opposed second distal end. Additionally, the light source guide element may include a channel extending away from the central body for receiving the light source conductor. The channel may include a tubular passageway for holding a first light source conductor. Further, a first light source conductor may be retained by a light source guide element. The first light source conductor may extend along the first interfacing prong toward the opposed first distal end and the opposed second distal end. Further still, the attachment arm may be configured to interface with a mounting structure and include at least one mounting aperture extending through the attachment arm. Further still, the first interfacing prong may include a proximal end adjoining the central body and an opposed distal end, wherein the opposed distal end includes a first width and the proximal end includes a second width. The second width may be wider than the first width for frictionally securing the rotational stabilizing locking mechanism to the inner arcuate blade. Also, a first curvature of a portion of at least one of the outer arcuate blade and the inner arcuate blade may match a second curvature of the central body. Additionally, the first interfacing prong may be configured to travel along the first prong slot until seated therein providing a pressure fitting between the inner arcuate blade and the first interfacing prong and rotationally locking in place the central body relative to the inner arcuate blade.

In yet another particular embodiment, a method to rotate the rotatable cone device is disclosed. The method includes A further embodiment includes a method of using a surgical retractor. The method may include providing and an outer arcuate blade, an inner arcuate blade and a rotational stabilizing locking mechanism. The outer arcuate blade may include a first proximal end and an opposed first distal end. Also, the outer arcuate blade may include a coupling aperture and the inner arcuate blade may include a first prong slot forming a gap extending through a full thickness of the inner arcuate blade. The inner arcuate blade may also include a second proximal end and an opposed second distal end. The inner arcuate blade may further include a coupling tab. Further, the rotational stabilizing locking mechanism may include a central body and a first interfacing prong extending from the central body. The method may involve inserting the coupling tab of the inner arcuate blade inside the coupling aperture of the outer arcuate blade. Also, the method may drive the first interfacing prong partly into the first prong slot. Once the interfacing prong is at least partly in the prong slot, the rotational stabilizing locking mechanism may be able to rotate from a first position to a second position, wherein the inner arcuate blade rotates relative to the outer arcuate blade. The method may further include driving the first interfacing prong fully into the first prong slot providing a pressure fitting between the inner arcuate blade and the first interfacing prong and rotationally locking the central body relative to the inner arcuate blade and the outer arcuate blade. Further still, the method may include constricting the first prong slot in order to allow the coupling tab to be inserted in the coupling aperture. Also, rotation of the rotational stabilizing locking mechanism may cause the coupling tab to slide within the coupling aperture. Additionally, the method may include emitting light from a first light source conductor extending from the central body toward a remote distal end of the first interfacing prong.

Further embodiments may include various means for performing functions corresponding to the method operations discussed herein.

BRIEF DESCRIPTION OF DRAWINGS

The accompanying drawings are presented to aid in the description of embodiments of the disclosure and are provided solely for illustration of the embodiments and not limitation thereof.

FIG. 3 is a side elevation view of a locking cap in accordance with an embodiment.

FIG. 4 is a top plan view of the locking cap of FIG. 3.

FIG. 5 is a bottom plan view of the locking cap of FIG. 3.

FIG. 11 is a top plan view of the inner arcuate blade of FIG. 10.

FIG. 12 is a bottom plan view of the inner arcuate blade of FIG. 10

FIG. 13 is a side elevation cross-sectional view of the inner arcuate blade at B-B of FIG. 11.

DETAILED DESCRIPTION

Figure 1:
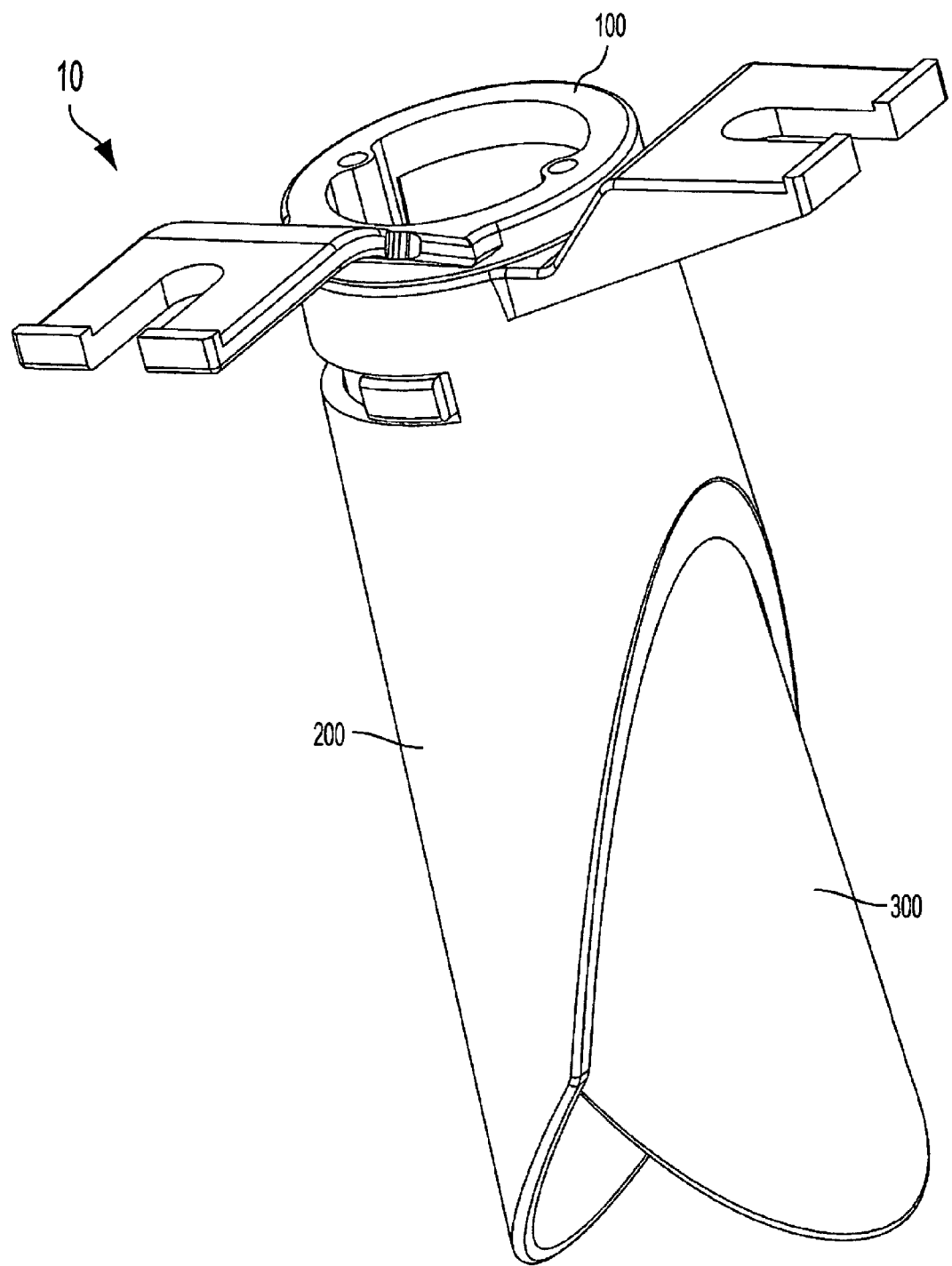
FIG. 1 is a perspective view of a surgical retractor with rotational stabilizing locking cap in accordance with an embodiment.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

The word "exemplary" is used herein to mean "serving as an example, instance, or illustration." Any implementation described herein as "exemplary" is not necessarily to be construed as preferred or advantageous over other implementations. Additionally, use of the words "first" and "second" or similar verbiage is intended herein for clarity purposes to distinguish various described elements and is not intended to limit the invention to a particular order or hierarchy of elements.

The word "mechanism" as used herein refers to a thing made or adapted for a particular purpose, especially a device with discrete parts and/or integral elements that work together. A mechanism may include a single unitary part or a plurality of parts. Additionally, the terms "mechanism," "device" and "apparatus" are used herein interchangeably.

The word "proximal" as used herein refers to an element or part thereof situated near or in closer proximity to a particular point or region of reference, such as a point of attachment. The accompanying figures that include a side elevation view should be understood to have a proximal end at the top of the illustrated element for the orientation shown. The word "distal" as used herein refers to the opposite of proximal and thus includes an element situated away from a particular point or region of reference. Thus, the accompanying figures that include a side elevation view should be understood to have a distal end at the bottom of the illustrated element for the orientation shown.

The word "aperture" as used herein refers to an opening, hole or gap passing entirely through a material or portion of a structure. Also, the word "slot" as used herein refers to an elongate narrow aperture or slit in a portion of a material element. Further, the word "passageway" as used herein refers to a duct or channel that may include a closed tubular form or includes a lengthwise opening. A passageway need not have a uniform, symmetric or simple geometric cross-sectional shape.

In an embodiment a rotational stabilizing locking apparatus functions by rotational displacement of an associated inner arcuate structure relative to an outer arcuate structure, such as two concentric blades adapted to function as a surgical refractor. The movement of the inner arcuate structure relative to the outer arcuate structure, once in position adjacent the tissue of a patient, may displace that tissue and provide an artificial passage and/or orifice for a surgical instrument. In accordance with an aspect of the disclosed technologies, the inner and outer arcuate structures may be inserted and reconfigured within a patient, so that a surgeon may control the extent of rotation between the two arcuate structures and preserve the integrity of the temporary passage and/or orifice thereby created. A rotational stabilizing locking apparatus in the form of a locking cap is hereby disclosed that may provide control of the extent of rotation and may lock the inner and outer arcuate blades relative to one another. Also, the locking cap may provide a channel for guiding a light source into the surgical cavity formed when the arcuate structures are deployed within a patient.

FIG. 1 illustrates a perspective view of an exemplary surgical retractor assembly 10 that includes a rotational stabilizing locking apparatus. The surgical retractor assembly 10 includes a locking cap 100, an outer arcuate blade 200 and an inner arcuate blade 300. The outer and inner arcuate blades 200, 300 are arcuate structures that together form a surgical retractor tool for providing access to a surgical cavity. In this illustrative embodiment, the upper portions of the outer and inner arcuate blades 200, 300 are conical, with the inner arcuate blade nested inside the outer arcuate blade. The lower portions of the arcuate blades 200, 300 may also be conical but have an opening formed on a bias relative to an axial center of the blades. While this embodiment shows the two blades as conical members, at least one of the two blades may include a lengthwise slit or gap that extends across the length of the entire blade. Thus, although the arcuate blades 200, 300 are illustrated as truncated conical or semi-cylindrical members, their arcs need not complete a circumference. The arcuate shape of the nested blades, with the use of the locking cap 100 as a manipulating tool, allows the inner arcuate blade 300 to be rotated relative to the outer arcuate blade 200. In the orientation shown in FIG. 1 the outer and inner arcuate blades 200, 300 are rotated into an open position. Also, the locking cap 100 once fully inserted into the position shown in FIG. 1 frictionally engages the inner arcuate blade 200 in such a way that both arcuate blades 200, 300 are rotationally secured relative to one another.

Figure 2:
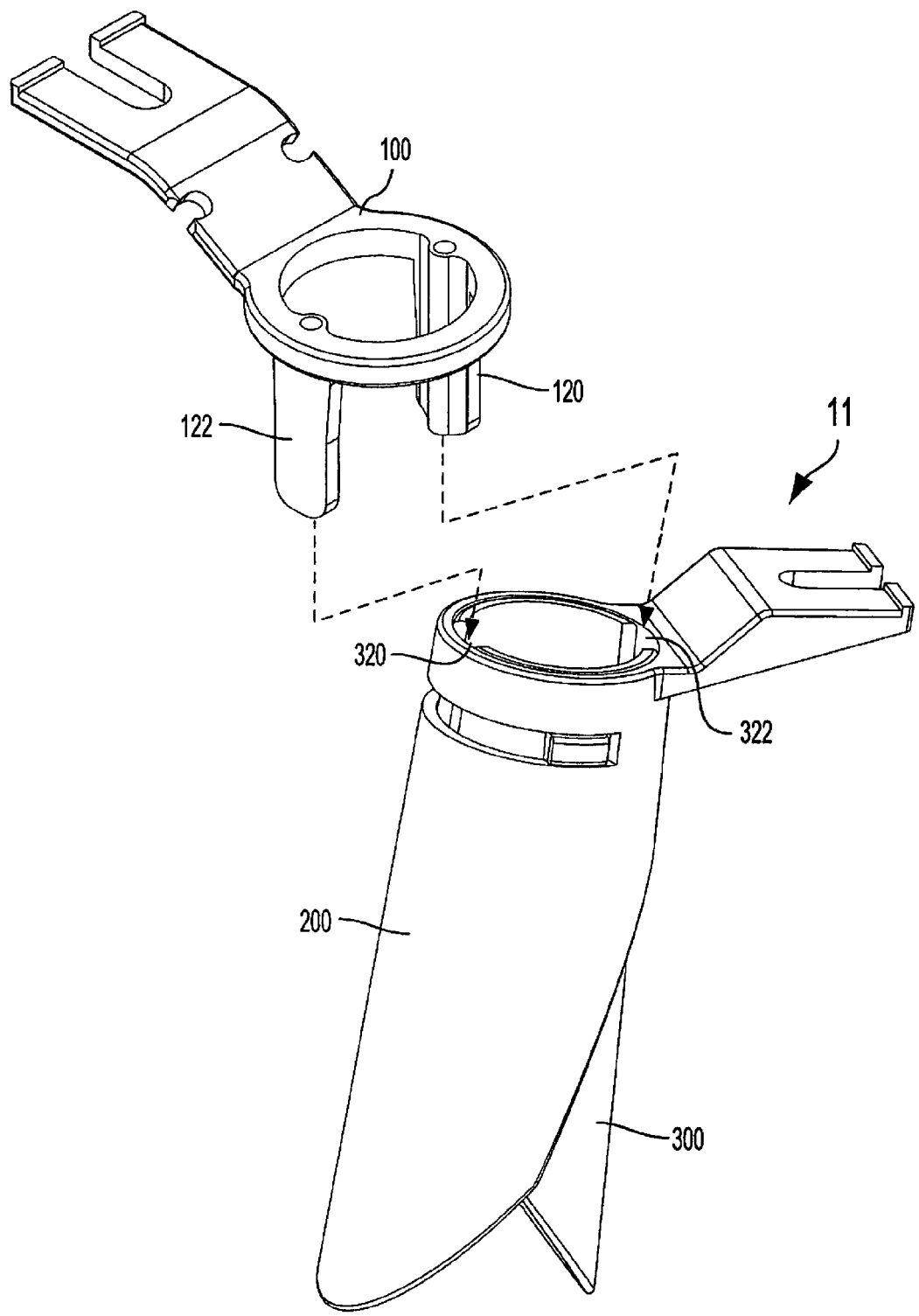
FIG. 2 is a partially exploded perspective view of the surgical retractor of FIG. 1.
Figure 6:
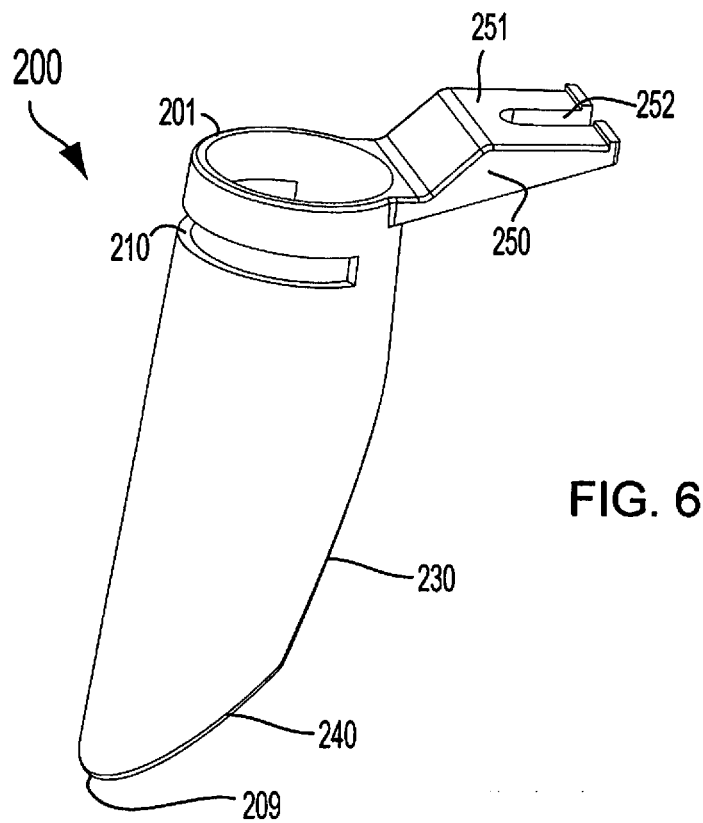
FIG. 6 is a perspective view of a surgical retractor outer arcuate blade in accordance with an embodiment.
Figure 7:
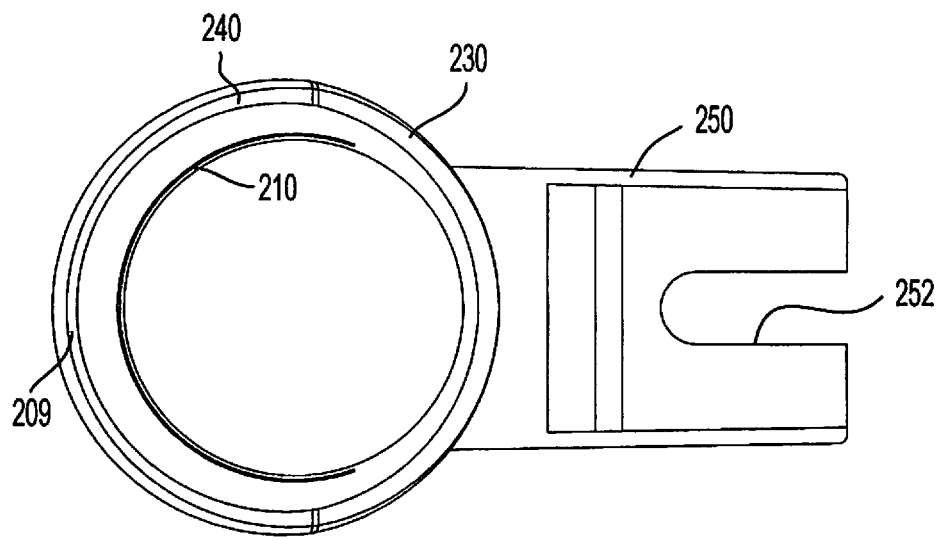
FIG. 7 is a bottom plan view of the outer arcuate blade of FIG. 6.
Figure 8:
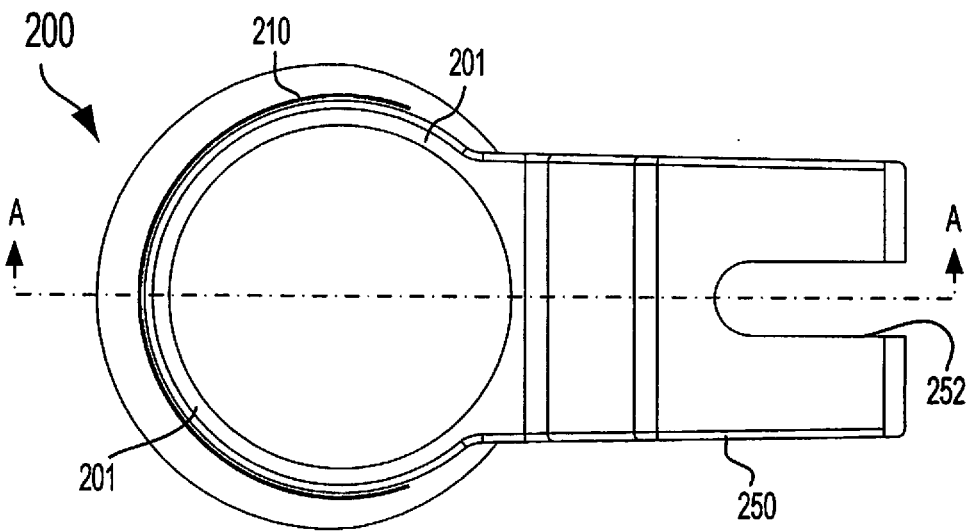
FIG. 8 is a top plan view of the outer arcuate blade of FIG. 6.

FIG. 2 illustrates a partially exploded perspective view of the locking cap 100 separated from the outer and inner arcuate blades 200, 300. The locking cap 100 includes two interfacing prongs 120, 122 that may be inserted into opposed prong slots 320, 322 of the inner arcuate blade 300. The locking cap 100 may be manipulated to provide control of the relative positions of the arcuate blades 200, 300 relative to one another. The outer and inner arcuate blades 200, 300 are together referred to as the surgical retractor 11. In the orientation shown, the surgical retractor 11 is in an open position since the distal (lowest) portions of the two blades 200, 300 are positioned opposite one another. The two blades 200, 300 may be rotated relative to one another into a closed position where the distal portions are immediately adjacent one another. It should be understood that the locking cap 100 may be inserted in the surgical retractor 11 when it is in a closed position, an open position or somewhere in between.

FIGS. 3-5 illustrate further details of the locking cap 100 of FIGS. 1 and 2. The locking cap 100 includes a central body 110 portion, centrally disposed between an attachment arm 130 and the interfacing prongs 120, 122. FIG. 3 shows a side elevation view of the locking cap 100. In the orientation shown, one interfacing prong 122 is shown extending from the bottom side of the central body 110. It should be understood that the opposed interfacing prong 120 (not shown) also extends from the bottom side of the central body 110 parallel to interfacing prong 122. The locking prongs 122 may be configured to integrate with the arcuate blades of the surgical retractor in such a way that the downward pressure of the locking prong 122 may force the various components to brace against one another and effectively lock the entire system. The removal of the rotational stabilizing locking mechanism 100 unlocks the system. Further detail of the interfacing prong 122 is visible with regard to its tapered width, which varies from the prong proximal end 123 to the opposed distal end 124. The interfacing prong 122 includes a first width $W_1$ at the distal end 124 and a second width $W_2$ at the proximal end 123. The first width $W_1$ may be narrower than the second width $W_2$. Also, a lower portion of the interfacing prongs 120, 122 may have a constant width and a taper to a larger width may begin somewhere near the center along the lengthwise extent of the prongs 120, 122. As described more fully below, the first and second widths $W_1$, $W_2$ provide a frictional locking feature when fully inserted into the surgical retractor assembly. As the first width $W_1$ of the interfacing prong 122 is initially inserted into the prong slot 322, the distal end 124 of the interfacing prong 122 may fit easily and smoothly into the prong slot 322 of the inner arcuate blade 300. Then, as the interfacing prong 122 is inserted further into the prong slot 322 and the proximal end 123 reaches the prong slot 322 the wider second width $W_2$ should provide more than just a snug fit in the prong slot to 322. In fact, the wider second width $W_2$ should bias apart the prong slot 322, thus providing a frictional locking of the entire assembly. The other interfacing prong 120 (shown in FIG. 2) may also include a similar varied width or may include a constant width for an embodiment having a reduced frictional locking.

Also, extending from the central body 110 is the attachment arm 130. Rather than extend from the bottom of the central body 100, the attachment arm 130 extends from the side of the central body 110. As shown in FIGS. 4 and 5, the attachment arm 130 may include a mounting slot 132. The mounting slot 132 may be configured to attach and/or integrate various other components, while preserving the functionality of a locking cap 100 and the surgical retractor arcuate blades 200, 300. The mounting slot 132 may be adapted to integrate with one or more table mounts (not shown). Such table mounts may be assembled and/or constructed around a patient to help stabilize and maintain static select instrumentation. Additionally, the attachment arm 130 may include at least one mounting aperture 134. As described in an exemplary embodiment below the mounting apertures 134 may be used for retaining cables, wires or other accessories used with surgical retractors.

FIGS. 4 and 5 show the central body 110 formed as an annular ring, which forms a surgical aperture 115 centrally disposed for preserving the surgeon's line of sight and an inner curvature of the surgical aperture 115 may be made to match and inner curvature of a proximal end of the inner arcuate blade 300. In this way, when the locking cap 100 is fully seated atop the outer and inner arcuate blades 200, 300 the central body 110 does not block line of sight through the inner space of the inner arcuate blade 300. Alternatively, the central body 110 may form an incomplete ring or broken ring, with gaps for example on the side opposite the extension arm 130. Additionally, the locking cap 100 may include a light source guide element 118 extending along a lengthwise extent of at least one of the interfacing prongs 120, 122 (i.e., a first light source guide element on one prong and a second light source guide element on the other prong). The light source guide 118 provides a channel or tubular passageway for conveying and/or guiding supplementary instruments, such as light sources, cameras, and suction tools, into a surgical cavity. These supplementary instruments may then be anchored to one or more mounting apertures 134 to prevent the wiring from blocking or obstructing the surgical aperture 115 and surrounding areas. FIGS. 4 and 5 also show that the light source guide 118 may contain a light source conductor 119, such as a fiber-optic cable. Where a light source conductor 119 is provided, a source of light may be placed adjacent to an upper side of the central body 110 directly above the light source conductor 119 in order to direct light through the interfacing prong, into the inner portion of the inner arcuate blade 300 and preferably into any surgical cavity that lies distally beyond.

FIGS. 6-9 illustrate further details of the outer arcuate blade 200 of FIGS. 1 and 2. In the orientation shown in FIGS. 6 and 9, the outer arcuate blade 200 includes a generally truncated conical shape at least in its central portion. Starting from the proximal end 201, which is formed as an annular end, the truncated cone-shape gets wider as it extends toward the distal end of the outer arcuate blade 200. The truncated cone-shape on the proximal end 201 may have an annular shape that matches the annular ring shape of the central body 110 of the locking cap 100. The proximal end may also include a supplemental attachment arm 250, which generally extends laterally from the proximal end 201. Additionally, the supplemental attachment arm 250 may include its own mounting slot 252, similar to mounting slot 132 of the locking cap 100. In this way, the mounting slot 252 may be configured to attach and/or integrate various other complements and/or adapted to integrate with one or more table mounts (not shown). Also, an upper surface profile 251 of the supplemental attachment arm 250 may have a similar and standardized size and/or configuration to that of the locking cap 100 attachment arm 130 in order to provide a uniform mounting surface.

Figure 9:
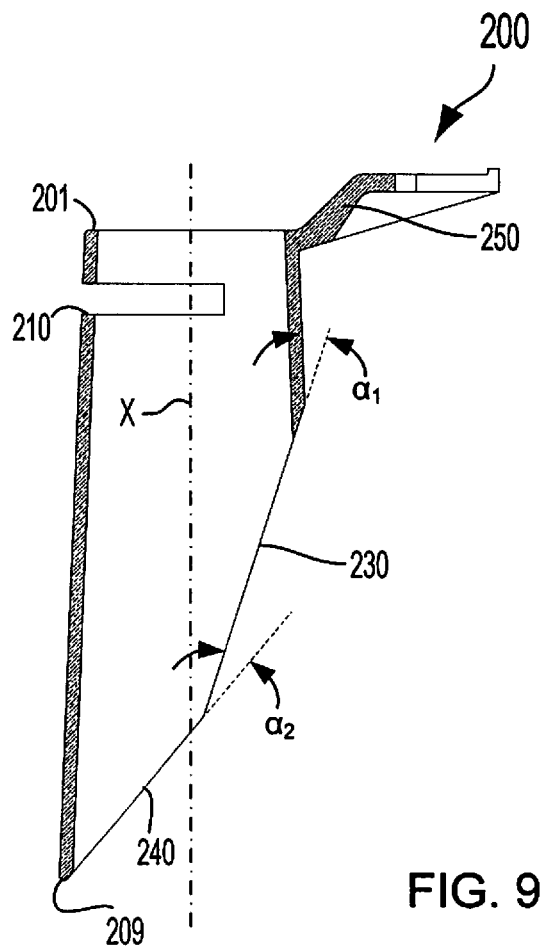
FIG. 9. is a side elevation cross-sectional view of the outer arcuate blade at A-A of FIG. 8.

The opposite side of the outer arcuate blade 200 may include one or more angled truncations. In this embodiment, the arcuate blade 200 includes two angled truncations 230, 240. The angled truncations 230, 240 form inclined surfaces 230, 240 along lower edges of the outer arcuate blade 200 that may serve to cut through and/or separate tissue when inserted into a patient. An angled truncation refers to a terminal portion of the otherwise conical shape that has a planar cut at an angle somewhere between perpendicular and parallel to a central longitudinal axis X (shown in FIG. 9) of the conical shape. The non-perpendicular angle may be measured from that central longitudinal axis X or from the angled outer surface of the conically shaped portion. FIG. 9, which is a section view at A-A of FIG. 8, also shows a first angle $\alpha_1$ of the first angled truncation 230, measured from an outer surface of the conical portion to an imaginary plane extending from the first angled truncation 230. Additionally, a second angle $\alpha_2$ of the second angled truncation 240 may be measured from a surface of the first angled truncation 230 to an imaginary plane extending from the second angled truncation 240. As shown the second angled truncation 240 extends to the distal end 209 of the outer arcuate blade 200. The first and second angles $\alpha_1$, $\alpha_2$ may be the same or varied as desired.

Additionally, the outer arcuate blade 200 may include a tab slot 210, formed as an aperture extending through a lateral wall of an upper conical portion. The tab slot 210 may extend approximately 180° around the upper conical portion of the outer arcuate blade 200 relative to a central longitudinal axis X. Such a central longitudinal axis is illustrated as a vertical line in the configuration shown in FIG. 9. From the bottom and top views of the outer arcuate blade 200, illustrated in FIGS. 7 and 8 respectively, the tab slot 210 is visible almost as simply an arched curve on the outer and inner surfaces of the conical shape. In this exemplary embodiment, the tab slot 210 extends more than 180° around the outer arcuate blade 200.

Figure 10:
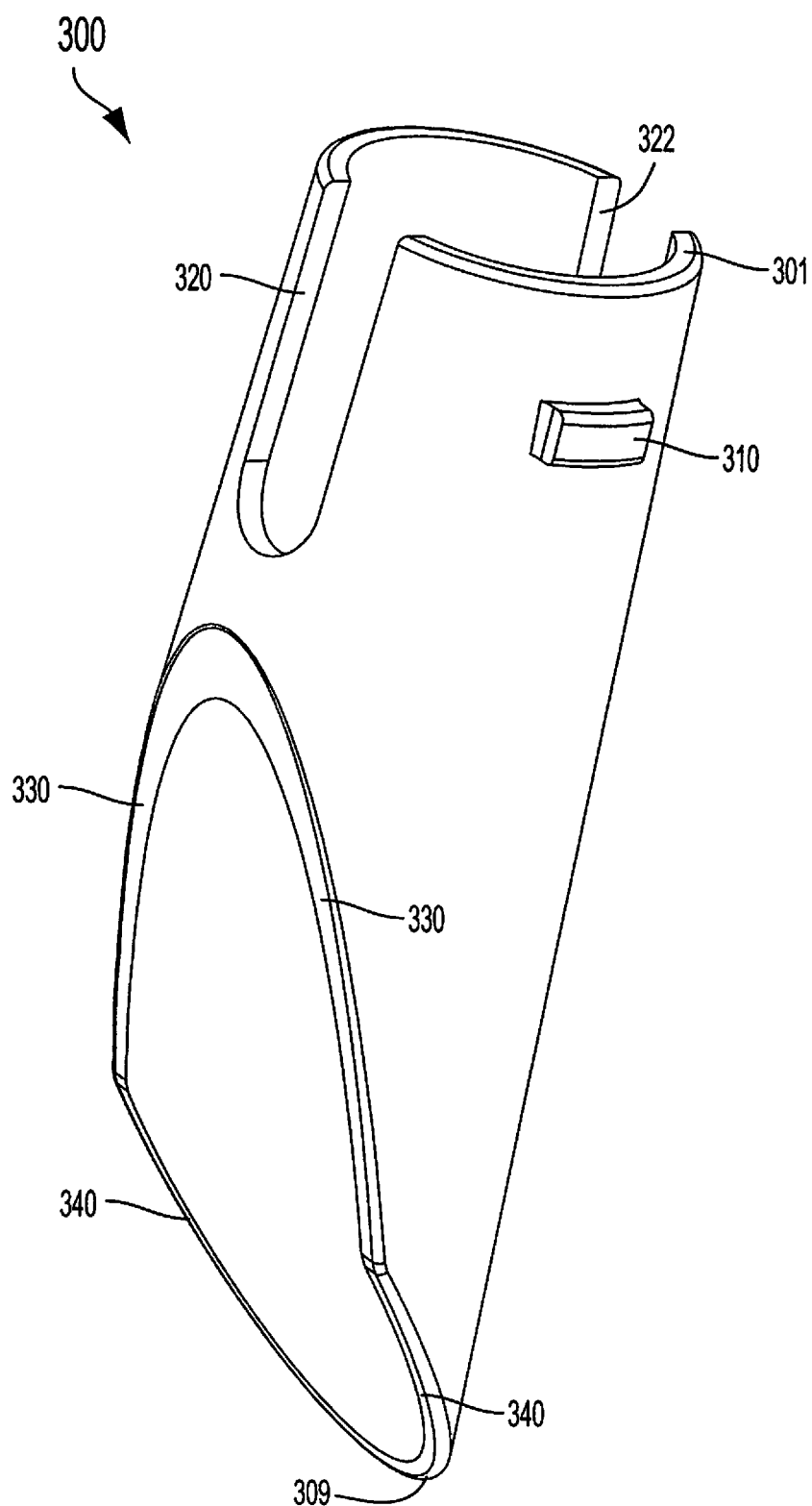
FIG. 10 is a perspective view of a surgical retractor inner arcuate blade in accordance with an embodiment.

FIGS. 10-13 illustrate further details of the inner arcuate blade 300 of FIGS. 1 and 2. The inner arcuate blade 300 may include a complementary truncated conical shape as to that of the outer arcuate blade 200. In this way, a distal portion of the inner arcuate blade 300 may include a first angled truncation 330 and a second angled truncation 340 that match the angled truncations 230, 240 of the outer arcuate blade 200. Similarly, the inner arcuate blade 300 may include a proximal end 301 and a distal end 309 that align respectively with the proximal end 201 and a distal end 209 of the outer arcuate blade 200. Additionally, the inner arcuate blade 300 may include a coupling tab 310 that is configured to be seated within the tab slot 210 when the two blades are nested. While the coupling tab 310 is disposed on one side of the inner arcuate blade 300 (as seen in FIG. 10), it may have alternatively been disposed on the opposite side. Also, a proximal portion of the inner arcuate blade 300 includes prong slots 320, 322 configured to receive the interfacing prongs 120, 122 of the locking cap 100. Each prong slot forms a gap (i.e., a first gap and a second gap, respectively) extending through a full thickness of the inner arcuate blade.

FIG. 11, which is a top view of the inner arcuate blade 300, also shows an upper portion inner arcuate wall 315 of the inner arcuate blade 300. The curvature of the upper portion inner arcuate wall 315 (i.e., a first curvature) may match a curvature of the surgical aperture 115 (i.e., a second curvature), particularly since the locking cap 100 may be configured to be mounted atop the inner arcuate blade 300, as described further below. The upper portion inner arcuate wall 315 may be the narrowest portion of the inner arcuate blade 300, as noted from the bottom view in FIG. 12.

The inner arcuate blade 300 may be made of a general flexible and resilient material, which may be at least slightly deformed with pressure, yet will spring back to its original shape once the pressure is released. The tab slots 320, 322 may enhance that flexibility and resiliency by allowing the proximal portion of the inner arcuate blade 300 to be contracted when the interfacing prongs 120, 122 are not yet inserted therein. FIG. 13, which is a section view at B-B of FIG. 11, shows a side view of one table slot 322. When the proximal portion of the inner arcuate blade 300 is radially compressed, at least an upper portion of the tab slots 320, 322 may narrow, allowing a corresponding upper portion of the inner arcuate blade 300 to compress.

Figure 14:
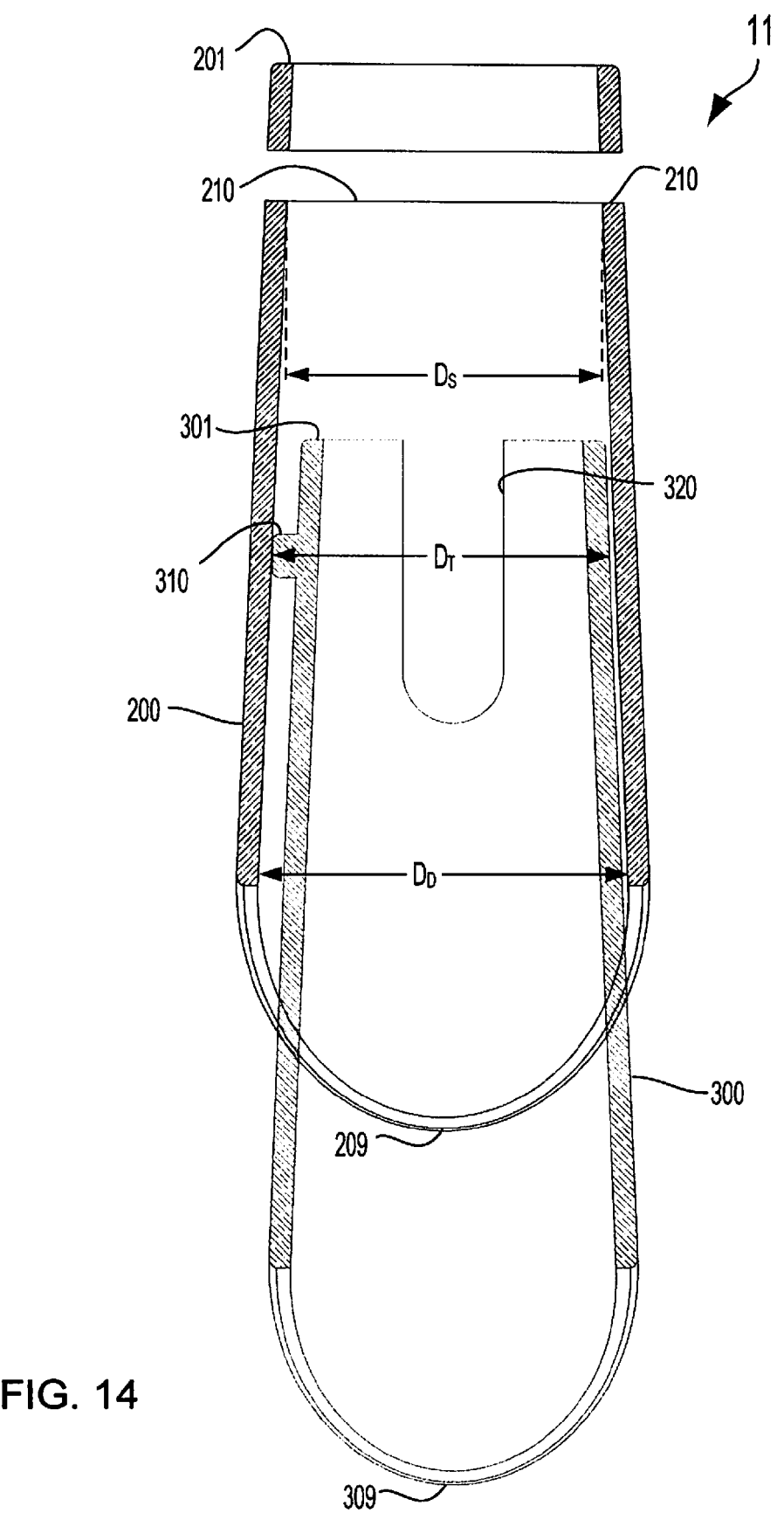
FIG. 14 is a side elevation cross-sectional view of the inner arcuate blade of FIG. 10 partially inserted inside the outer arcuate blade of FIG. 6.
Figure 15:
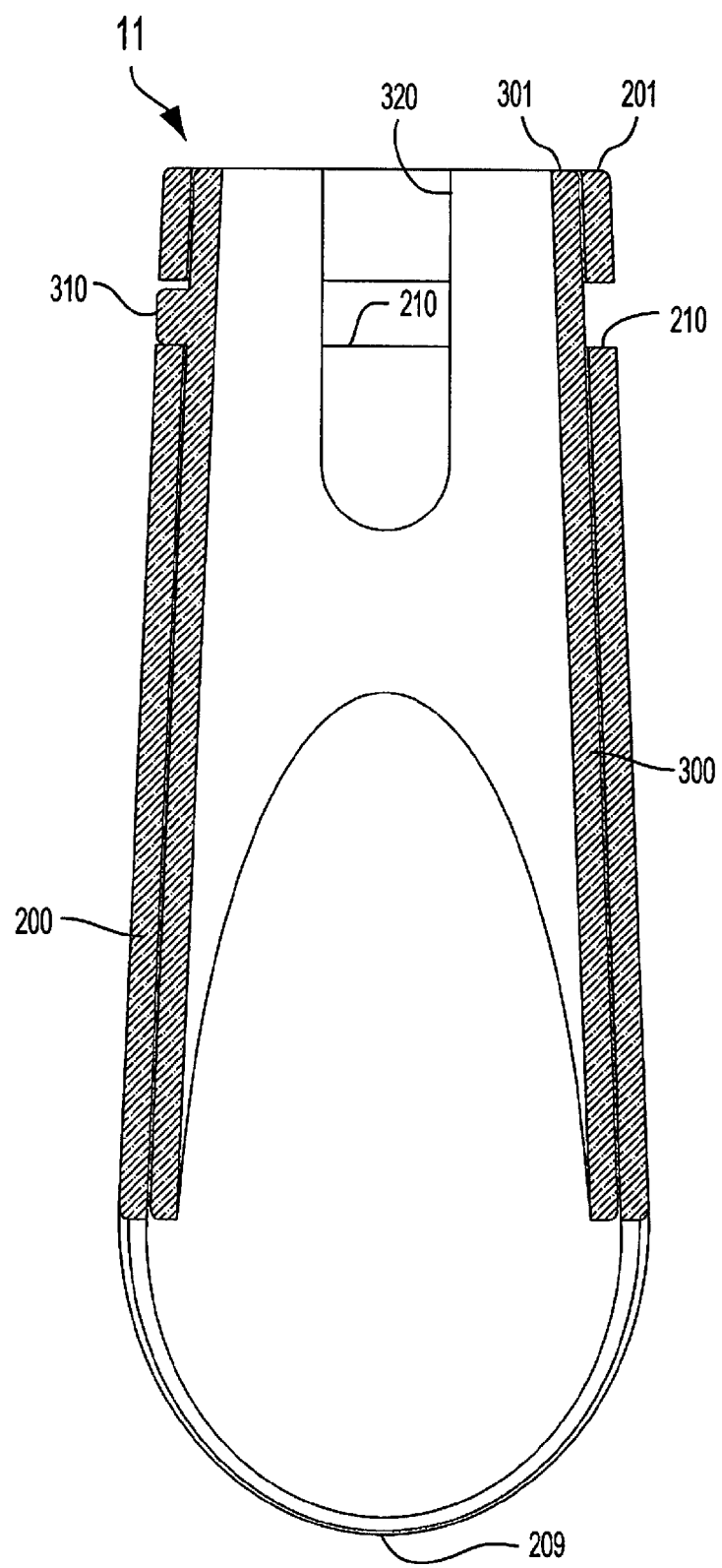
FIG. 15 is a side elevation cross-sectional view of the inner arcuate blade of FIG. 10 fully inserted inside the outer arcuate blade of FIG. 6.

FIGS. 14 and 15 illustrate how an inner arcuate blade 300 may be inserted into an outer arcuate blade 200 to form an embodiment surgical retractor 11. The outer arcuate blade 200 includes an opening at both a first proximal end 201 and a first distal end 209. Also, since the outer arcuate blade 200 is generally conical shaped, the opening at the first proximal end 201 is narrower than the opening at the first distal end 209. The inner arcuate blade 300 has a similar shape to the outer arcuate blade 200, but sized smaller such that the inner arcuate blade 300 may fit nested inside the outer arcuate blade. In accordance with an aspect of the disclosed technologies, the second distal end 309 is wider than the first proximal end 201. Thus, in order to nest the two blades together, as shown in FIG. 15, the outer arcuate blade 300 must be inserted with its second proximal end 301 first through the second distal end 209 of the outer arcuate blade 200 toward the first distal end 201. When the two blades are fully nesting, an outer diameter of the second proximal end 301 may fit just inside an inner diameter of the opening in the first proximal end 201. Similarly, an outer surface of an arched curve formed by the second distal end 309 may fit just inside an inner surface of an arched curve formed by the first distal end 209.

The two blades 200, 300 may be restricted from simply and easily nesting with one anther, due to the coupling tab 310 protruding laterally from the side of the inner arcuate blade 300. Due to the narrowing conical shape of the blades, an inner diameter $D_S$ of the outer arcuate blade 200 near the proximal end (i.e., near the top in the orientation shown in FIGS. 14 and 15) is smaller than an outer diameter $D_T$ of the inner arcuate blade 300 where the coupling tab 310 is disposed (referred to herein as the tab diameter $D_T$). Thus, without partially deforming at least the second proximal end 301, the inner arcuate blade 300 is restricted from being fully inserted inside the outer arcuate blade 200 due to the protruding coupling tab 310. The tab diameter $D_T$ may be smaller than a distal opening inner diameter $D_D$ of the outer arcuate blade 200, allowing the inner arcuate blade 300 to be easily inserted inside at least the distal end of the outer arcuate blade 200. In particular, the inner arcuate blade 300 needs to be squeezed in order to be inserted far enough inside the outer arcuate blade 200 to allow the coupling tab 310 to reach the tab slot 210. Hence, the at least one prong slot 320, 322 in the inner arcuate blade 300 is provided to allow the second proximal end 301 to deform slightly. The prong slots 320, 322 form a gap extending through a full thickness of the second proximal end 301. In this way, the second proximal end 301 may be squeezed slightly (not shown), thus contracting a width of at least an upper portion of the prong slot 320, as well as the temporary tab diameter $D_{Temp}$, allowing the coupling tab 310 to reach the coupling aperture 210. Once the coupling tab 310 reaches the coupling aperture 210, the second proximal end 301 may resiliently expand from its temporarily contracted state so the coupling tab 310 is seated inside the coupling aperture 210, as shown in FIG. 15. In this way, the mating arrangement of the tab slot 210 and the coupling tab 310 hold the two blades together in a nested arrangement. Additionally, as described further below the tab slot 210 serves to limit rotation of the inner arcuate blade 300 relative to the outer arcuate blade 200.

Figure 16:
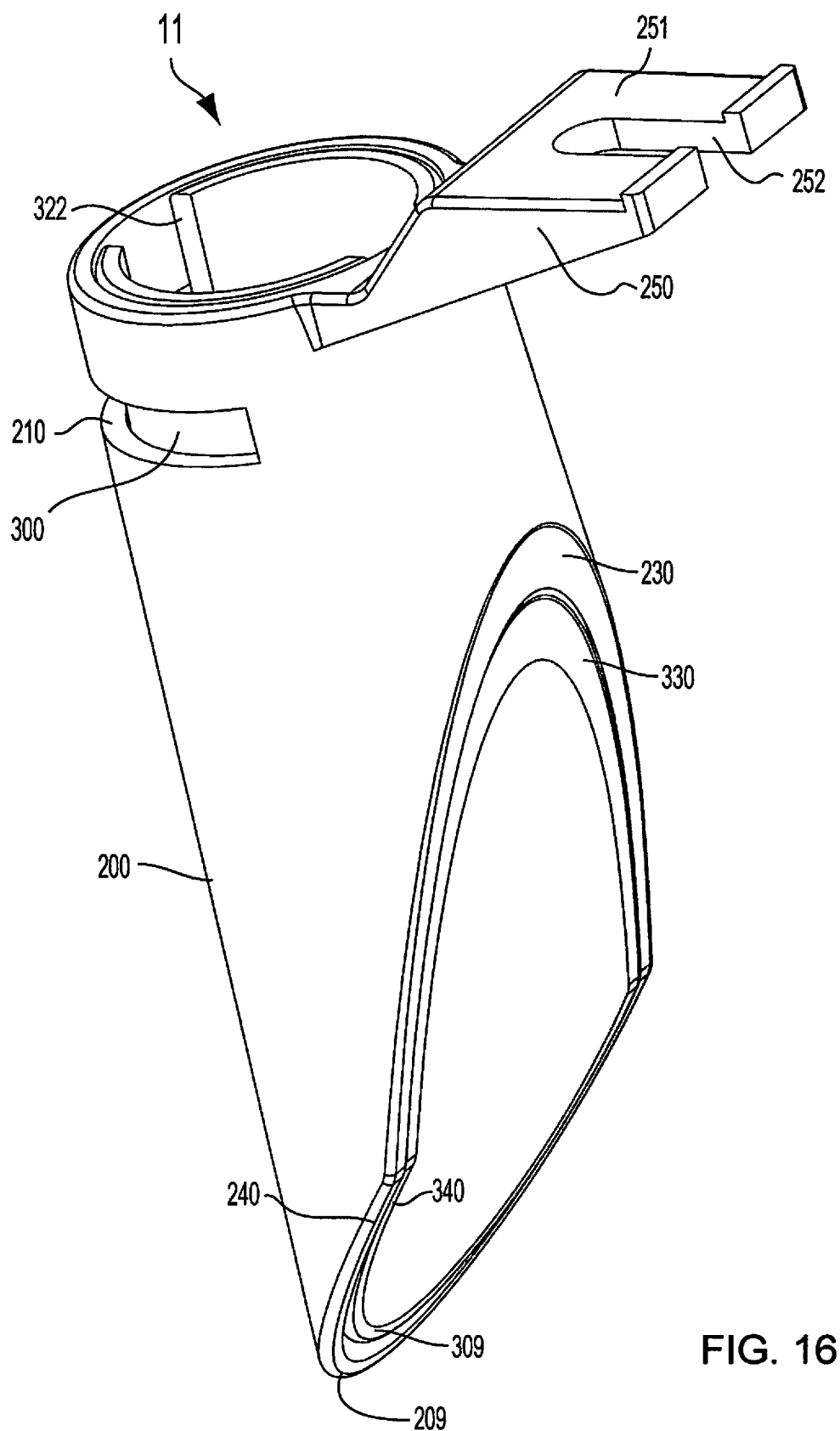
FIG. 16 is a perspective view of the inner arcuate blade of FIG. 10 fully inserted inside the outer arcuate blade of FIG. 6 forming a surgical retractor and with inner and outer arcuate blades rotated into alignment.

FIG. 16 illustrates a perspective view of a surgical retractor 11 including an inner arcuate blade 300 fully seated within an outer arcuate blade 200. In the position shown, the outer and inner arcuate blades 200, 300 are said to be in alignment and/or in a "closed position." The outer and inner arcuate blades 200, 300 also serve as a surgical refractor. In the closed position the arcuate blades 200, 300 together have a smaller profile, which may minimize the invasive insertion of such a tool into a patient. Eventually, when the inner arcuate blade 300 is rotated relative to the outer arcuate blade 200 into an open position (as shown in FIGS. 1 and 2), the combined arcuate blades 200, 300 exhibit a wider profile particularly at the lower end. This wider profile is used to separate tissue and maintain a passage and/or cavity for a surgical procedure. Also shown in FIG. 16 is how the planar surfaces formed by the first angled truncations 230, 330 of the inner and outer arcuate blades 200, 300 lie in the same plane when in the closed position. Similarly, the second angled truncations 240, 340 of the inner and outer arcuate blades 200, 300 lie in the same plane when in the closed position.

Figure 17:
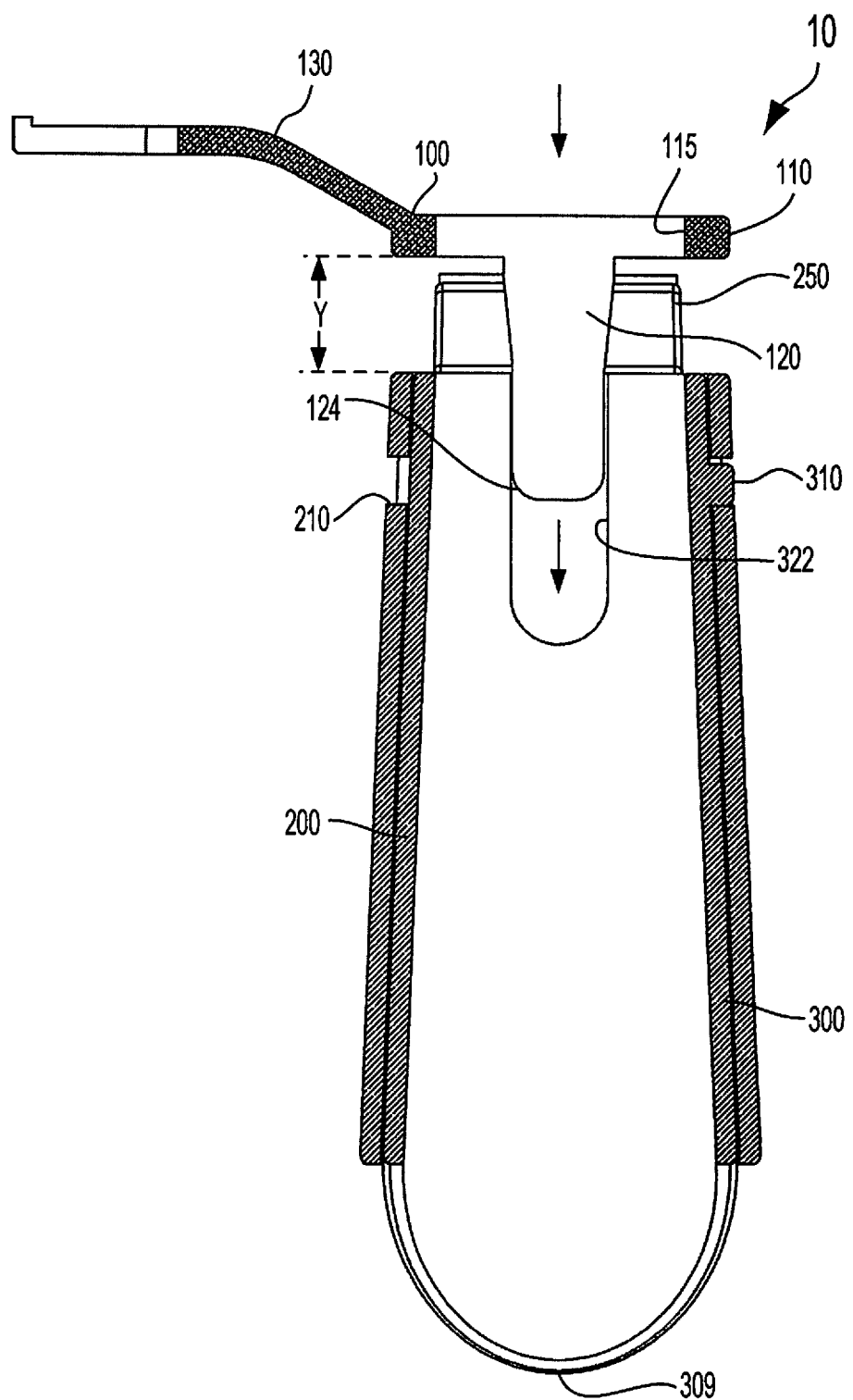
FIG. 17 is a side elevation cross-sectional view of a locking cap partially inserted into an inner arcuate blade already inserted into an outer arcuate blade in accordance with an embodiment.

Once the inner and outer arcuate blades 200, 300 are nested as shown in FIG. 16 the locking cap 100 may be used to rotate and/or lock the two blades together rotationally and axially. FIG. 17 illustrates a side elevation cross-sectional view of a surgical retractor assembly 10 in accordance with an embodiment. In FIG. 17 the locking cap 100 is partially inserted atop the nested blades 200, 300. As shown, the locking prongs 120, 122 are inserted almost half way into the respective prong slots 320, 322, leaving an offset Y between the proximal ends 201, 301 of the blades 200, 300 and the closer side of the central body portion 110 of the locking cap 100. As long as only the lower narrower width $W_1$ portions of the locking prongs 120, 122 are inserted in the prong slots 320, 322, the locking cap 100 may be said to be in the partially inserted position. In the partially inserted position, the locking cap 100 may be rotated relative to the outer arcuate blade 200 and the inner arcuate blade 300 will similarly rotate. In this way, a surgeon may rotate the surgical refractor between the closed and open positions. FIG. 17 shows the two blades 200, 300 in an open position since the distal end 209 of the outer arcuate blade 200 is not visible. Rotating 180° the locking cap 100, from the configuration shown in FIG. 17, would cause the attachment arm 130 to extend to the right, rather than to the left as shown. Also, the locking tab 310 would similarly switch sides due to the rotation. Thus, in the process of rotating the rotational stabilizing locking mechanism (i.e., the locking cap 100) the coupling tab 310 slides within the coupling aperture 210. In this way, the width of the coupling aperture 210 around the outer arcuate blade 200 may limit how far the inner and outer arcuate blades 200, 300 may rotate relative to one another.

Figure 18:
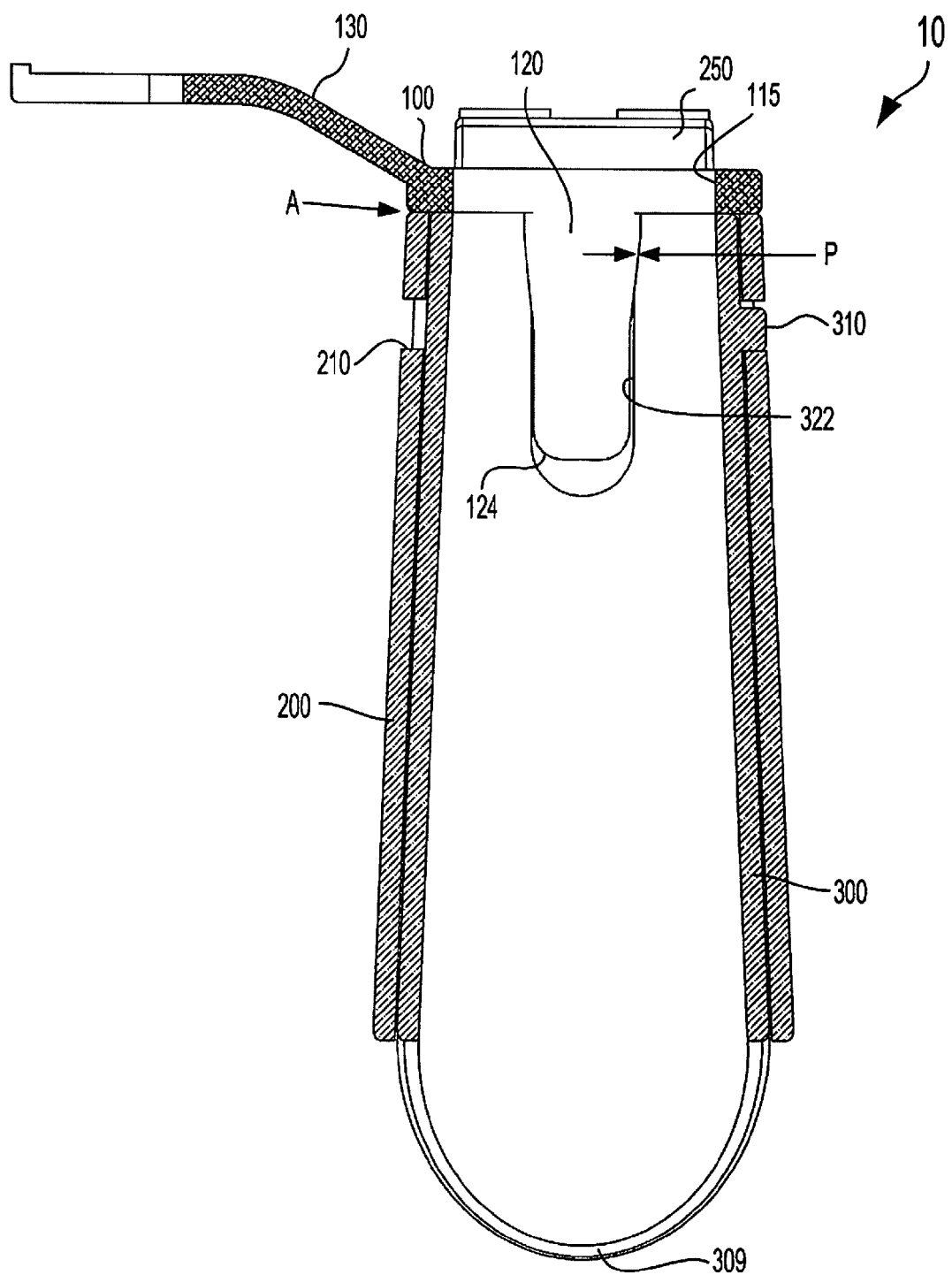
FIG. 18 is a side elevation cross-sectional view of a locking cap fully inserted into an inner arcuate blade already inserted into an outer arcuate blade in accordance with an embodiment.

FIG. 18 illustrates another side elevation cross-sectional view of a surgical retractor assembly 10 in accordance with an embodiment. In contrast to FIG. 17, in FIG. 18 the locking cap 100 is fully inserted atop the nested blades 200, 300. As noted at A, the offset Y has been eliminated. However, the offset Y need not be fully eliminated, it just needs to be reduced enough to pressure-lock the assembly 10. Once the wider width $W_2$ portions of the locking prongs 120, 122 engage the sides of the prong slots 320, 322, an outward pressure P will be exerted on the prong slots 320, 322 encouraging at least an upper portion of the inner arcuate blade 300 to expand slightly. That outward pressure P will in-turn create pressure between the two blades 200, 300, which will result in the surgical retractor assembly 10 being pressure locked. Once pressure locked, the two blades 200, 300 may neither rotate relative to one another nor move relative to one another axially. In this way, a surgeon may ensure the surgical retractor stays in either a closed or open position, as desired.

Figure 19:
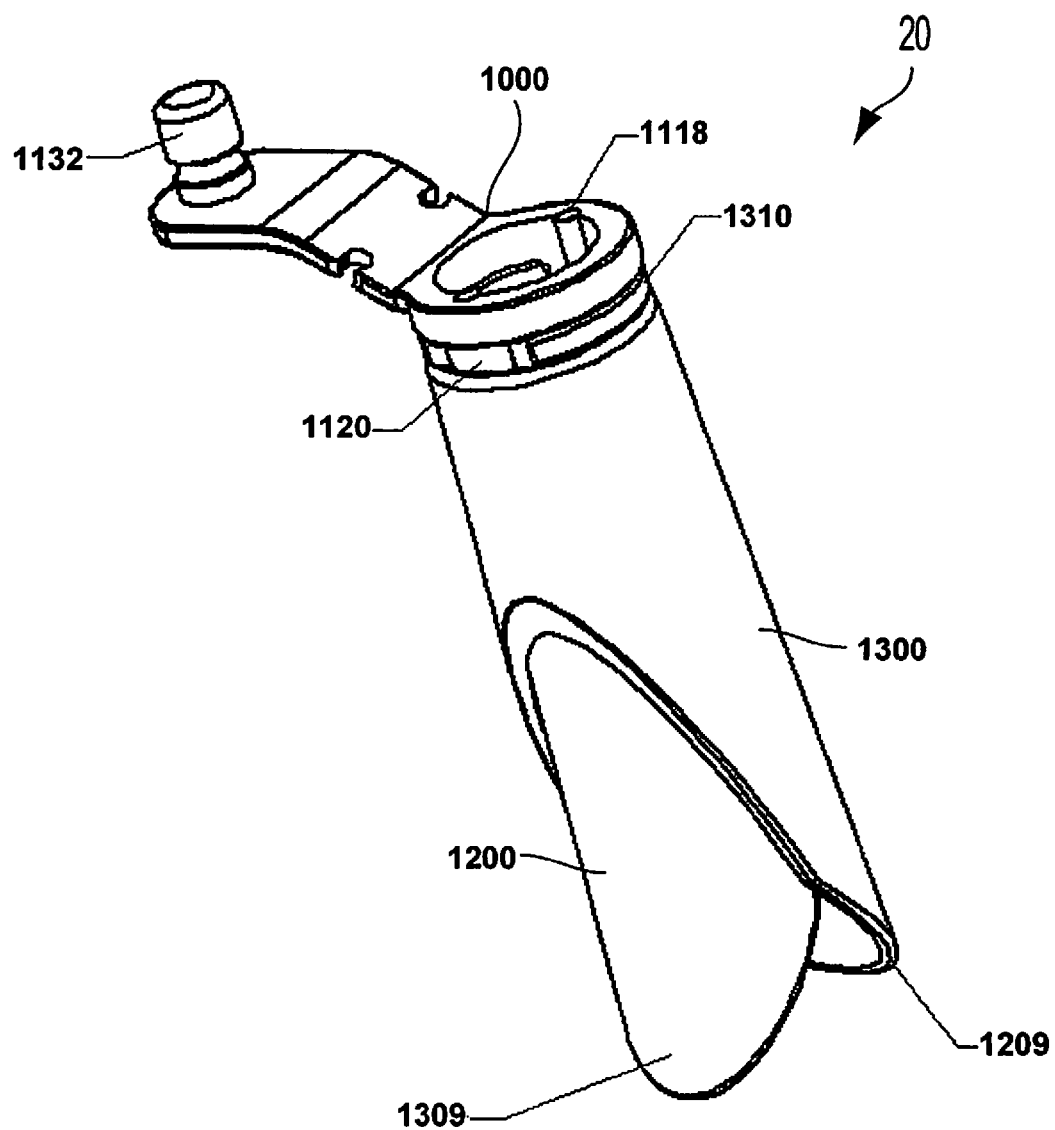
FIG. 19 is a perspective view of an alternative surgical retractor with rotational stabilizing locking cap in accordance with another embodiment.

FIG. 19 illustrates another embodiment surgical retractor assembly 20, shown in a perspective view. Once again the surgical retractor assembly 20 includes a locking cap 1000, an outer arcuate blade 1200 and an inner arcuate blade 1300. The surgical retractor assembly 20 is shown in the open position with the distal ends 1209, 1309 of the surgical retractor blades 1200, 1300 rotated opposite one another. One distinction from the previous embodiment is that rather than providing a tab slot for a locking tab, the inner blade 1300 includes a radially protruding flange 1310 that sits on top of the proximal end of the outer blade 1200.

Figure 20:
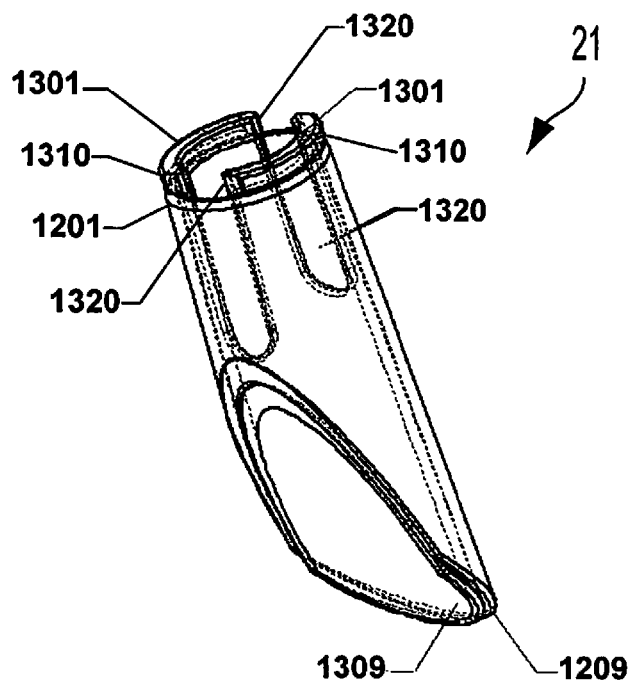
FIG. 20 is a perspective view of the surgical refractor of FIG. 19 with the locking cap removed and with inner and outer arcuate blades rotated into alignment.
Figure 21:
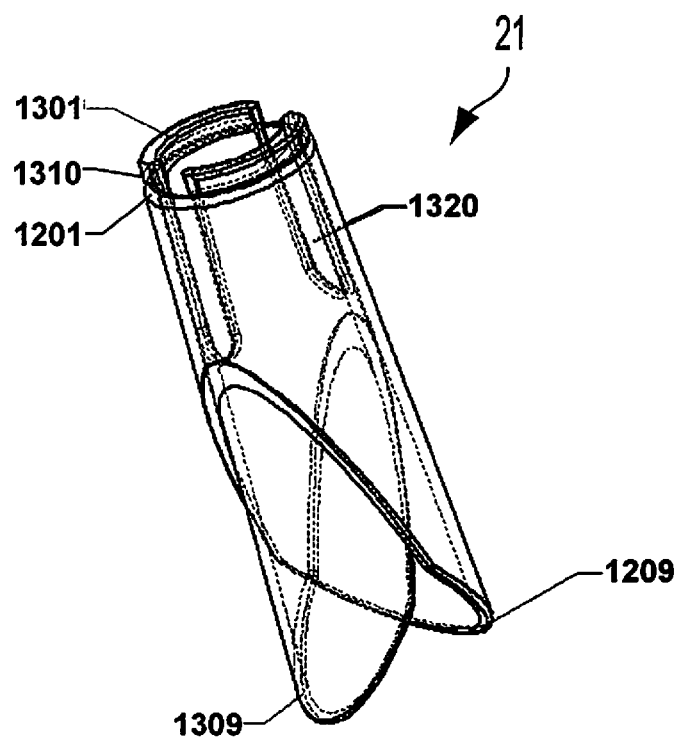
FIG. 21 is a perspective view of the surgical refractor of FIG. 19 with the locking cap removed and with inner and outer arcuate blades rotated out of alignment.

FIGS. 20 and 21 illustrate further perspective views of the inner and outer blades 1200, 1300 forming a surgical retractor 21, with the locking cap 1000 removed. FIG. 20 shows the closed position, wherein the distal portions 1209, 1309 of the blades are immediately adjacent one another. In contrast, FIG. 21 shows the open position, wherein the distal portions 1209, 1309 of the blades are rotated and disposed remote and opposite one another. Also, without the locking cap 1000, the inner blade 1300 proximal end 1301 and the radially protruding flange 1310 are more clearly visible resting above the outer blade 1200 proximal end 1201. As with the previous embodiment, as the inner blade 1300 is inserted up into the outer blade 1200, a proximal (i.e., upper) portion of the inner blade 1300 compresses. Namely, the prong slots 1320 may get somewhat smaller as a biasing force of being forced against an inner conical surface of the outer blade 1200. Once the inner blade 1300 is fully nested inside the outer blade 1200, the entire protruding flange 1310 snaps radially outwardly and locks the two blades 1200, 1300 from separating axially (i.e., in the vertical direction per the orientation shown in the drawings).

Figure 22:
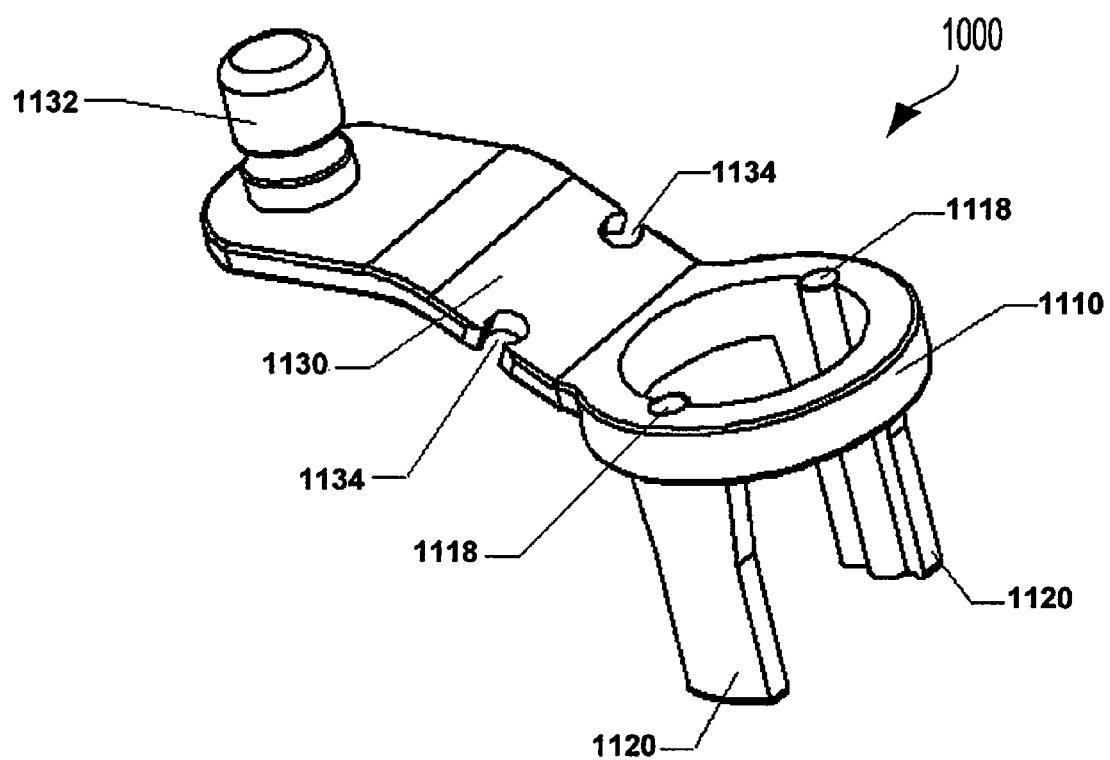
FIG. 22 is a perspective view of the alternative locking cap of FIG. 19.

FIG. 22 illustrates the alternative locking cap 1000 without the surgical retractor blades 1200, 1300. This perspective view shows elements similar to the previous embodiment include a central body 1110, an attachment arm 1130, mounting apertures 1134, light source guides 1118 and interfacing prongs 1120. The locking cap 1000 further includes a mounting pin 1132, which is an alternative to the mounting slot of the previous embodiment.

Figure 23:
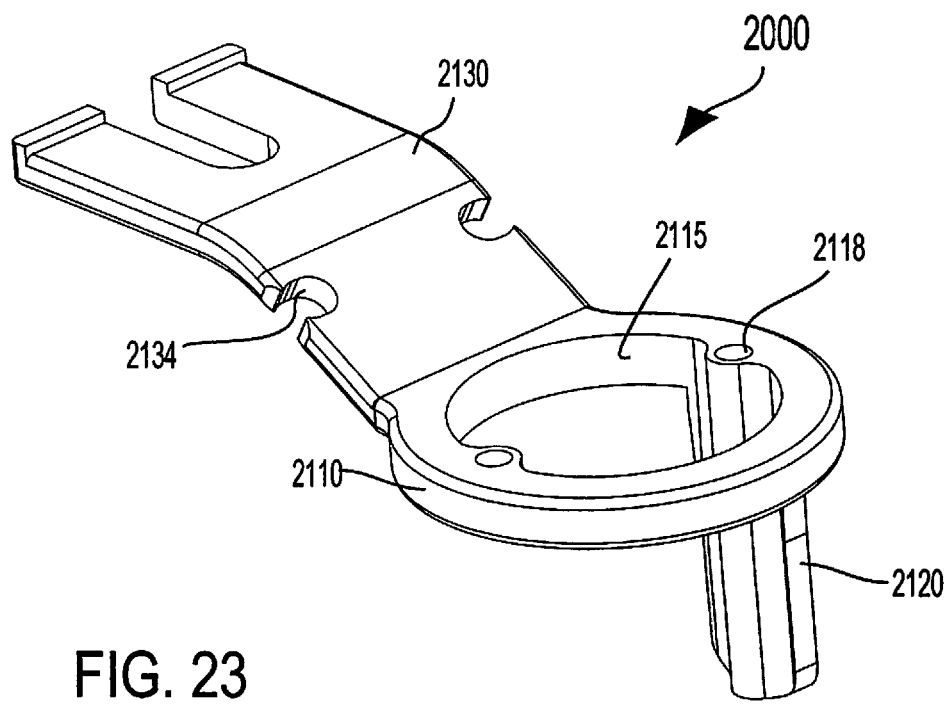
FIG. 23 is a perspective view of a further alternative locking cap in accordance with another embodiment.
Figure 24:
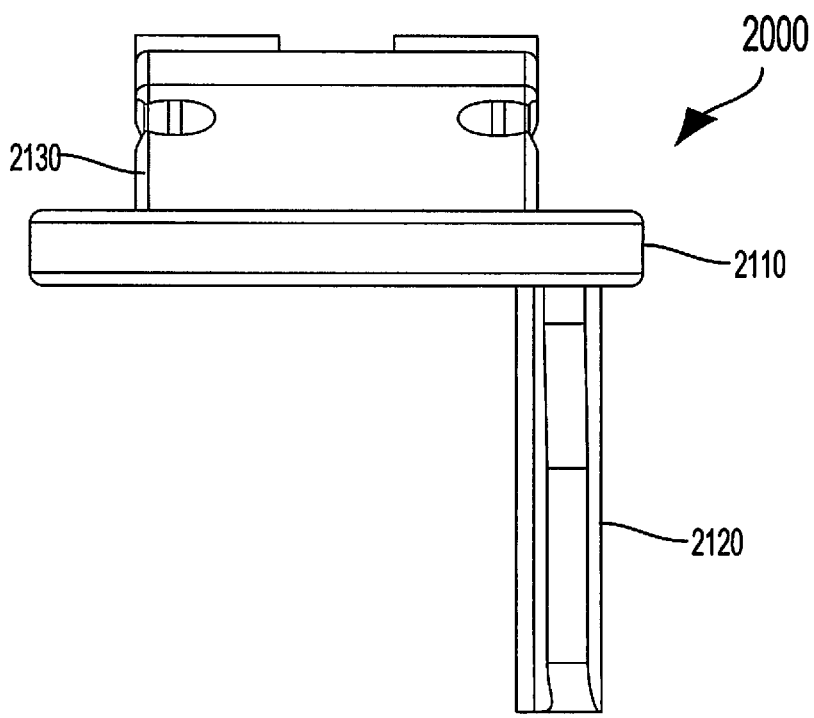
FIG. 24 is a front elevation view of the locking cap of FIG. 23.

FIGS. 23 and 24 illustrate another alternative locking cap 2000. Once again, this cap 2000 includes a central body 2110, an attachment arm 2130, mounting apertures 2134 and at least one light source guide 2118. In fact, this locking cap 2000 is very similar to the first embodiment with one notable exception. That exception is that this locking cap 2000 includes only one interfacing prong 1120. Using this cap 2000 only one prong slot is needed. Thus, the surgical retractor blade(s) only need one prong slot to work with this cap 2000. It will work with an inner arcuate blade having two prong slots, but only one would be used at a time so the surgeon may chose from the two.

In various embodiments, the dimensions of the surgical retractor assemblies 10, 20 or the individual elements may be modified as desired. The particular proportional sizes shown in the accompanying drawings are for illustrative purposes. As an example of dimensions for an embodiment locking cap central body 110 may be between approximately 10 mm and 80 mm in length. Also the first and second interfacing prongs 120, 126 may extend between approximately 3 mm and 150 mm. Further, the locking caps 100, 1000, 2000, inner arcuate blade(s) 200, 1200 or outer arcuate blade(s) 300, 1300 may be made of a material such as a polymer, metal, ceramic, biological material, or composite. Such materials may maintain rigid pressure between the locking cap 100 and surgical retractor blades. For example, the surgical retractor assemblies 10, may be made of aluminum. Other materials and combinations of materials may be used as desired.

Figure 25:
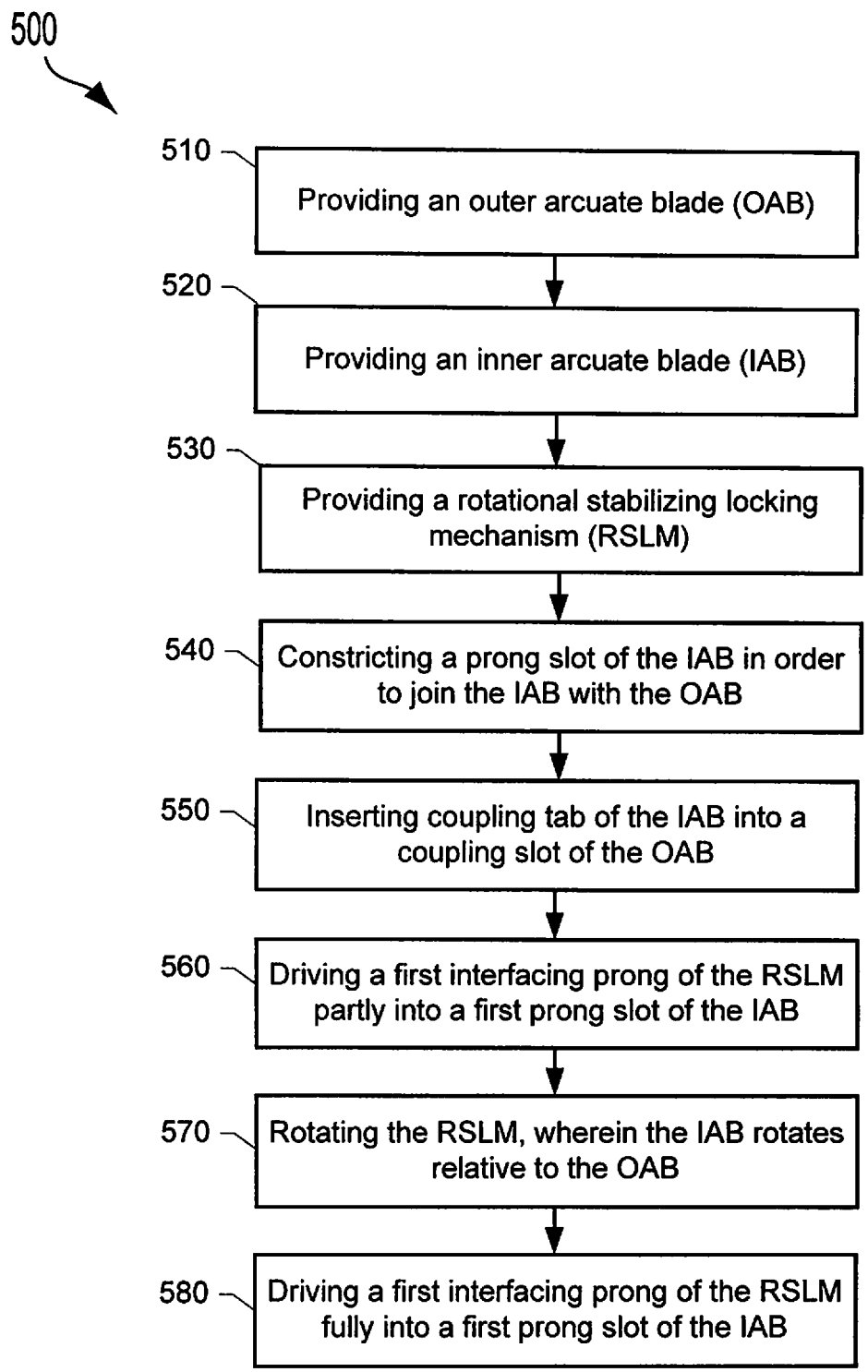
FIG. 25 is a process flow of a method of using a surgical retractor in accordance with an embodiment.

FIG. 25 illustrates a process flow for an embodiment method 500 of using a surgical retractor. At block 510, the method may include providing and an outer arcuate blade (OAB). The OAB may include a first proximal end, an opposed first distal end and a coupling aperture. Exemplary embodiments of OAB's are described above with regard to the outer arcuate blades 200, 1200. Additionally, at block 520, the method may include providing and an inner arcuate blade (IAB). The inner arcuate blade may include at least one prong slot forming a gap extending through a full thickness of the inner arcuate blade. For example, a first prong slot and an offset second prong slot may be provided. Also, the inner arcuate blade may include a second proximal end, an opposed second distal end and a coupling tab. Exemplary embodiments of IAB's are described above with regard to the inner arcuate blades 300, 1300. Also, at block 530 the method may include providing a rotational stabilizing locking mechanism (RSLM). The RSLM may include a central body and a first interfacing prong extending from the central body. Exemplary embodiments of RSLM's are described above with regard to the locking cap 100, 1000, and 2000. These early method elements, 510, 520, and 530 may be accomplished in virtually any order. In block 540, a prong slot of the at least one prong slot in the IAB may be constricted in order to join and fix in an axial direction the IAB with the OAB. Also, block 550 includes inserting the coupling tab of the inner arcuate blade inside the coupling aperture of the outer arcuate blade. The description associated with FIGS. 14 and 15 above provide further exemplary details in regard to how the coupling tab on the IAB reaches and may be seated within the coupling aperture in the OAB. In block 560 the first interfacing prong may be driven partly into the first prong slot. Once the first interfacing prong is properly positioned, in block 570 the RSLM may be rotated from a first position to a second position. The first and second positions may correspond to the open and closed positions referred to above with regard to the surgical retractor. The rotation in block 570 may be from open to closed positions or closed to open, as desired. Once rotated into the desired position, in block 580 the first interfacing prong of the RSLM may be fully inserted into the first prong slot of the IAB.

Additionally, although not shown in the process flow of FIG. 25, the method may further include driving the first interfacing prong fully into the first prong slot providing a pressure fitting between the inner arcuate blade and the first interfacing prong and rotationally locking the central body relative to the inner arcuate blade and the outer arcuate blade. Additionally, the aspect of rotating the RSLM in block 570 may include sliding the coupling tab within the coupling aperture. Further, the method may include emitting light from a first light source conductor extending from the central body toward a remote distal end of the first interfacing prong.

The foregoing method descriptions and the process flow diagrams are provided merely as illustrative examples and are not intended to require or imply that the blocks of the various embodiments must be performed in the order presented. As will be appreciated by one of skill in the art the order of blocks in the foregoing embodiments may be performed in any order.

Words such as "thereafter," "then," "next," etc. are not intended to limit the order of the blocks; these words are simply used to guide the reader through the description of the methods. Further, any reference to claim elements in the singular, for example, using the articles "a," "an" or "the" is not to be construed as limiting the element to the singular. The word "exemplary" is used herein to mean "serving as an example, instance, or illustration." Any implementation described herein as "exemplary" is not necessarily to be construed as preferred or advantageous over other implementations.

The various illustrative logical blocks, modules, and process flow diagram blocks described in connection with the embodiments disclosed herein may be implemented as an apparatus manipulated by human hand. Alternatively, electronic hardware, computer software, or combinations of both may manipulate the apparatus. To clearly illustrate this interchangeability of hardware and software, various illustrative components, blocks, modules, circuits, and blocks have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A rotational stabilizing locking apparatus for providing access to a surgical cavity, comprising:
    a central body including a surgical aperture extending from a first side of the central body to a second opposed side of the central body, the central body including an attachment arm extending away from the surgical aperture;
    a first interfacing prong extending from the first side of the central body;
    an outer arcuate blade including a first proximal end and an opposed first distal end; and
    an inner arcuate blade mounted within the outer arcuate blade, the inner arcuate blade including a prong slot forming a first gap in the inner arcuate blade, wherein the first interfacing prong is configured to travel along the prong slot until seated within the prong slot and disposed inward of the outer arcuate blade, wherein when seated within the prong slot the first interfacing prong causing an upper portion of the prong slot and the inner arcuate blade to expand rotationally locking the central body, the inner arcuate blade, and the outer arcuate blade relative to one another.

2. The rotational stabilizing locking apparatus of claim 1, further comprising:
    a second interfacing prong extending from the first side of the central body, the second interfacing prong disposed remote from the first interfacing prong.

3. The rotational stabilizing locking apparatus of claim 2, wherein the second interfacing prong includes a light source guide element extending lengthwise along the second interfacing prong.

4. The rotational stabilizing locking apparatus of claim 1, wherein the first interfacing prong includes a light source guide element along an extent of the first interfacing prong.

5. The rotational stabilizing locking apparatus of claim 4, wherein the light source guide element includes a channel extending away from the first side of the central body for receiving a first light source conductor, the channel includes a tubular passageway for holding the first light source conductor.

6. The rotational stabilizing locking apparatus of claim 4, further comprising:
    a light source conductor retained by the light source guide element, the light source conductor extending from the central body toward a remote distal end of the first interfacing prong.

7. The rotational stabilizing locking apparatus of claim 1 wherein the attachment arm is configured to interface with a mounting structure and includes at least one mounting aperture extending through the attachment arm.

8. The rotational stabilizing locking apparatus of claim 1, wherein the first interfacing prong includes a proximal end adjoining the central body and an opposed distal end, wherein the opposed distal end includes a first width and the proximal end includes a second width, the second width being wider than the first width and the upper portion of the prong slot before being caused to expand when the first interfacing prong is seated therein.

9. The rotational stabilizing locking apparatus of claim 8, wherein insertion of the second width of the first interfacing prong into the prong slot causes the upper portion of the prong slot and the inner arcuate blade to expand.

10. The rotational stabilizing locking apparatus of claim 1, wherein the outer arcuate blade includes a coupling aperture, wherein the inner arcuate blade includes a second proximal end and an opposed second distal end, the inner arcuate blade including a coupling tab configured to be disposed within the coupling aperture, the first proximal end and the second proximal end disposed adjacent the central body.

11. The rotational stabilizing locking apparatus of claim 10, wherein at least one of the first proximal end and the second proximal end include an annular shape.

12. The rotational stabilizing locking apparatus of claim 10, wherein the coupling tab prevents the inner arcuate blade from being fully inserted inside the outer arcuate blade without deforming at least one of the outer arcuate blade and the inner arcuate blade.

13. The rotational stabilizing locking apparatus of claim 12, wherein deforming at least one of the outer arcuate blade and the inner arcuate blade includes deforming the second proximal end by temporarily constricting the prong slot.

14. The rotational stabilizing locking apparatus of claim 10, wherein a curvature of the surgical aperture is sized to match an inner arcuate wall of the inner arcuate blade.

15. The rotational stabilizing locking apparatus of claim 1, wherein the outer arcuate blade and the inner arcuate blade each form a truncated conical shape, the inner arcuate blade being partially surrounded by the outer arcuate blade.

16. A surgical retractor with rotational stabilizing locking, comprising:
an outer arcuate blade including a first proximal end and an opposed first distal end, the outer arcuate blade including a coupling aperture;
an inner arcuate blade in sliding engagement with the outer arcuate blade, the inner arcuate blade including a first prong slot forming a first gap extending through a full thickness of the inner arcuate blade, the inner arcuate blade including a second proximal end and an opposed second distal end, the inner arcuate blade including a coupling tab configured to be disposed within the coupling aperture; and
a rotational stabilizing locking mechanism comprising,
a central body including a surgical aperture extending from a first side of the central body to a second opposed side of the central body, the central body including an attachment arm extending away from the outer arcuate blade and the inner arcuate blade; and
a first interfacing prong extending from the central body into the first prong slot, wherein when seated within the first prong slot the first interfacing prong causing an upper portion of the first prong slot and the inner arcuate blade to expand rotationally locking the rotational stabilizing locking mechanism, the inner arcuate blade, and the outer arcuate blade relative to one another.

17. The surgical retractor of claim 16, wherein the inner arcuate blade includes a second prong slot forming a second gap extending through the full thickness of the inner arcuate blade, the second prong slot disposed remote from the first prong slot, wherein the rotational stabilizing locking mechanism further comprising:
a second interfacing prong extending from the central body into the second prong slot.

18. The surgical retractor of claim 17, wherein at least one of the first interfacing prong and the second interfacing prong includes a light source guide element for retaining a light source conductor extending from the central body toward the opposed first distal end and the opposed second distal end.

19. The surgical retractor of claim 18, wherein the light source guide element includes a channel extending away from the central body for receiving the light source conductor.

20. The surgical retractor of claim 19, wherein the channel includes a tubular passageway for holding the light source conductor.

21. The surgical retractor of claim 16, further comprising:
a light source conductor retained by a light source guide element, the light source conductor extending along the first interfacing prong toward the opposed first distal end and the opposed second distal end.

22. The surgical retractor of claim 21, wherein the attachment arm is configured to interface with a mounting structure and includes at least one mounting aperture extending through the attachment arm.

23. The surgical retractor of claim 16, wherein the first interfacing prong includes a proximal end adjoining the central body and an opposed distal end, wherein the opposed distal end includes a first width and the proximal end includes a second width, the second width being wider than the first width, wherein insertion of the second width of the first interfacing prong into the first prong slot causes the upper portion of the first prong slot and the inner arcuate blade to expand.

24. The surgical retractor of claim 16, wherein a first curvature of a portion of at least one of the outer arcuate blade and the inner arcuate blade matches a second curvature of the central body.

25. The surgical retractor of claim 16, wherein at least one of the outer arcuate blade and the inner arcuate blade includes an annular end.

26. The surgical retractor of claim 16, wherein the outer arcuate blade and the inner arcuate blade each form a truncated conical shape, the inner arcuate blade being partially surrounded by the outer arcuate blade.

27. The surgical retractor of claim 26, wherein the coupling tab prevents the inner arcuate blade from being fully inserted inside the outer arcuate blade without deforming the second proximal end.

28. The surgical retractor of claim 27, wherein deforming the second proximal end includes temporarily constricting the first prong slot.

29. The surgical retractor of claim 16, wherein a curvature of the central body is sized to match an inner arcuate wall of the inner arcuate blade.

30. A method of using a surgical retractor, the method comprising:
providing and an outer arcuate blade, an inner arcuate blade and a rotational stabilizing locking mechanism, the outer arcuate blade including a first proximal end and an opposed first distal end, the outer arcuate blade including a coupling aperture, the inner arcuate blade including a first prong slot forming a gap extending through a full thickness of the inner arcuate blade, the inner arcuate blade including a second proximal end and an opposed second distal end, the inner arcuate blade including a coupling tab, the rotational stabilizing locking mechanism including a central body and a first interfacing prong extending from the central body, wherein the central body includes a surgical aperture extending from a first side of the central body to a second opposed side of the central body;
inserting the coupling tab of the inner arcuate blade inside the coupling aperture of the outer arcuate blade;
driving the first interfacing prong partly into the first prong slot;
rotating the rotational stabilizing locking mechanism from a first position to a second position, wherein the inner arcuate blade rotates relative to the outer arcuate blade; and
driving the first interfacing prong further into the first prong slot causing an upper portion of the first prong slot and the inner arcuate blade to expand rotationally locking the rotational stabilizing locking mechanism, the inner arcuate blade, and the outer arcuate blade relative to one another.

31. The method of using a surgical retractor of claim 30, further comprising:
constricting the first prong slot in order to allow the coupling tab to be inserted in the coupling aperture.

32. The method of using a surgical retractor of claim 30, wherein rotation of the rotational stabilizing locking mechanism, before driving the first interfacing prong into the first prong slot, causes the coupling tab to slide within the coupling aperture.

33. The method of using a surgical retractor of claim 30, further comprising:

emitting light from a first light source conductor extending from the central body toward a remote distal end of the first interfacing prong.

* * * * *